US009090563B2

(12) United States Patent
Vlahov et al.

(10) Patent No.: US 9,090,563 B2
(45) Date of Patent: Jul. 28, 2015

(54) BIVALENT LINKERS AND CONJUGATES THEREOF

(75) Inventors: Iontcho Radoslavov Vlahov, West Lafayette, IN (US); Christopher Paul Leamon, West Lafayette, IN (US); Apparao Satyam, Mumbai (IN); Stephen J. Howard, Springfield, IL (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 13/609,995

(22) Filed: Sep. 11, 2012

(65) Prior Publication Data

US 2013/0158271 A1   Jun. 20, 2013

Related U.S. Application Data

(63) Continuation of application No. 11/632,895, filed as application No. PCT/US2005/026068 on Jul. 22, 2005, now Pat. No. 8,288,557.

(60) Provisional application No. 60/590,580, filed on Jul. 23, 2004.

(51) Int. Cl.
| C07D 213/62 | (2006.01) |
| C07D 401/12 | (2006.01) |
| C07D 213/71 | (2006.01) |
| A61K 47/48 | (2006.01) |
| A61K 49/00 | (2006.01) |
| C07D 475/04 | (2006.01) |

(52) U.S. Cl.
CPC ........ C07D 213/71 (2013.01); A61K 47/48107 (2013.01); A61K 49/0002 (2013.01); C07D 401/12 (2013.01); C07D 475/04 (2013.01)

(58) Field of Classification Search
CPC ............................ C07D 213/71; C07D 401/12
See application file for complete search history.

(56) References Cited

U.S. PATENT DOCUMENTS

| 2,515,483 | A | 7/1950 | Wolf et al. |
| 2,816,110 | A | 12/1957 | Sletzinger et al. |
| 3,387,001 | A | 6/1968 | Hargrove et al. |
| 3,392,173 | A | 7/1968 | Hargrove et al. |
| 4,166,810 | A | 9/1979 | Cullinan et al. |
| 4,203,898 | A | 5/1980 | Cullinan et al. |
| 4,316,885 | A | 2/1982 | Rakhit |
| 4,337,339 | A | 6/1982 | Farina et al. |
| 4,639,456 | A | 1/1987 | Trouet et al. |
| 4,650,803 | A | 3/1987 | Stella et al. |
| 4,691,024 | A | 9/1987 | Shirahata et al. |
| 4,713,249 | A | 12/1987 | Schroder |
| 4,801,688 | A | 1/1989 | Laguzza et al. |
| 4,866,180 | A | 9/1989 | Vyas et al. |
| 4,870,162 | A | 9/1989 | Trouet et al. |
| 5,006,652 | A | 4/1991 | Cullinan et al. |
| 5,094,849 | A | 3/1992 | Cullinan et al. |
| 5,100,883 | A | 3/1992 | Schiehser |
| 5,108,921 | A | 4/1992 | Low et al. |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,138,051 | A | 8/1992 | Hughes et al. |
| 5,140,104 | A | 8/1992 | Coughlin et al. |
| 5,151,413 | A | 9/1992 | Caufield et al. |
| 5,169,851 | A | 12/1992 | Hughes et al. |
| 5,194,447 | A | 3/1993 | Kao |
| 5,221,670 | A | 6/1993 | Caufield |
| 5,233,036 | A | 8/1993 | Hughes |
| 5,258,389 | A | 11/1993 | Goulet et al. |
| 5,260,300 | A | 11/1993 | Hu |
| 5,266,333 | A | 11/1993 | Cady |
| 5,302,584 | A | 4/1994 | Kao et al. |
| 5,362,718 | A | 11/1994 | Skotnicki et al. |
| 5,378,696 | A | 1/1995 | Caufield |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,416,016 | A | 5/1995 | Low et al. |
| 5,417,982 | A | 5/1995 | Modi |
| 5,463,048 | A | 10/1995 | Skotnicki et al. |
| 5,491,231 | A | 2/1996 | Nelson et al. |
| 5,547,668 | A | 8/1996 | Kranz et al. |
| 5,552,545 | A | 9/1996 | Pearce et al. |
| 5,562,907 | A | 10/1996 | Arnon |
| 5,583,020 | A | 12/1996 | Sullivan |
| 5,627,165 | A | 5/1997 | Glazier |
| 5,635,382 | A | 6/1997 | Low et al. |

(Continued)

FOREIGN PATENT DOCUMENTS

| CA | 2372841 | 11/2000 |
| CA | 2376175 | 12/2000 |
| EP | 0 116 208 A1 | 8/1984 |
| EP | 0 163 550 A2 | 12/1985 |
| EP | 0 247 792 | 12/1987 |
| EP | 0116208 | 3/1988 |
| EP | 0 280 741 A1 | 9/1988 |
| EP | 0 354 728 | 2/1990 |
| JP | 59-175493 | 10/1984 |
| JP | 60-255789 | 12/1985 |

(Continued)

OTHER PUBLICATIONS

Zaragoza Dorwald, Side Reactions in Organic Synthesis, 2005, Wiley-VCH Verlag GmbH & Co. KGaA, Weinheim, Preface. p. IX.*

(Continued)

Primary Examiner — Paul A Zucker
(74) Attorney, Agent, or Firm — Barnes & Thornburg LLP

(57) ABSTRACT

Bivalent linkers to be included in or for preparing vitamin, drug, diagnostic agent, and/or imaging agent conjugates are described.

1 Claim, 4 Drawing Sheets

(56) References Cited

U.S. PATENT DOCUMENTS

| | | | |
|---|---|---|---|
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 * | 1/2002 | Zalipsky ............... 424/450 |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Molnar-Kimber et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 | 7/2010 | Hoefle et al. |
| 8,476,451 B2 | 7/2013 | Ellman et al. |
| 8,765,096 B2 | 7/2014 | Leamon |
| 2002/0151088 A1 | 10/2002 | Molnar-Kimber et al. |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Mancharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2009/0247914 A1 | 10/2009 | Manoharan et al. |
| 2010/0004276 A1 | 1/2010 | Vlahov et al. |
| 2010/0048490 A1 | 2/2010 | Vlahov et al. |
| 2010/0104626 A1 | 4/2010 | Leamon et al. |
| 2014/0249315 A1 | 9/2014 | Vlahov et al. |

FOREIGN PATENT DOCUMENTS

| | | |
|---|---|---|
| WO | WO/85/05554 | 12/1985 |
| WO | WO 88/01622 | 3/1988 |
| WO | WO 90/12096 | 10/1990 |
| WO | WO 91/07418 | 5/1991 |
| WO | WO95/15335 | 6/1995 |
| WO | WO96/36367 | 11/1996 |
| WO | WO 98/08859 | 3/1998 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74382 | 10/2001 |
| WO | WO02/059272 | 8/2002 |
| WO | WO 02/085908 | 10/2002 |
| WO | WO 02/087424 | 11/2002 |
| WO | WO 02/098868 | 12/2002 |
| WO | WO03/050295 | 6/2003 |
| WO | WO03/092742 | 11/2003 |
| WO | WO 03/097647 A1 | 11/2003 |
| WO | WO 2004/005326 | 1/2004 |
| WO | WO 2004/005327 | 1/2004 |
| WO | WO 2004/012735 | 2/2004 |
| WO | WO/2004/022099 | 3/2004 |
| WO | WO/2004/037210 | 5/2004 |
| WO | WO 2004/046170 | 6/2004 |
| WO | WO 2004/054622 | 7/2004 |
| WO | WO 2004/069159 A2 | 8/2004 |
| WO | WO2004/100983 | 11/2004 |
| WO | WO 2005/074901 | 8/2005 |
| WO | WO 2005/112919 | 12/2005 |
| WO | WO2005/115912 | 12/2005 |
| WO | WO 2006/012527 | 2/2006 |
| WO | WO 2006/042146 | 4/2006 |
| WO | WO/2006/089007 | 8/2006 |
| WO | WO 2006/101845 | 9/2006 |
| WO | WO2006/105141 | 10/2006 |
| WO | WO2007/002222 | 1/2007 |
| WO | WO 2007/022493 | 2/2007 |
| WO | WO 2007/022494 | 2/2007 |
| WO | WO2007/022512 | 2/2007 |
| WO | WO2007/140298 | 12/2007 |
| WO | 2008/057437 | 5/2008 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |
| WO | WO 2010/045598 | 4/2010 |
| WO | WO 2011/069116 | 6/2011 |
| WO | WO2011/106639 | 9/2011 |
| WO | WO2012/019123 | 2/2012 |

OTHER PUBLICATIONS

Senter et al, Journal of Organic Chemistry, Development of a Drug-Release Strategy Based on the Reductive Fragmentation of Benzyl Carbamate Disulfide, 1990, 55, pp. 2975-2978.*

U.S. Appl. No. 60/808,367, filed May 25, 2014, Vite et al.

(56) References Cited

OTHER PUBLICATIONS

Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.
Archer M.C. et al., "Separation of Folic Acid Derivatives and Pterins by High-Performance Liquid Chromatography," *Methods in Enzymology*, 1980; 66: pp: 452-459.
Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.
Ayers W.A., "Effect of Vitamin B12 and Analogs on the Respiration of a Marine Bacterium," *Archives of Biochemistry and Biophysics*, 1962, vol. 96, pp. 210-215.
Barnett C.J. et al., "Structure-Activity Relationships of Dimeric Catharanthus Alkaloids. 1. Deacetylvinblastine Amide (Vindesine) Sulfate," *J. Med Chem.* 21: 88-96 (1978).
Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.
Bavetsias, V., et al., "The design and synthesis of water-soluble analogues of CB30865, a quinazolin-4-one-based antitumor agent," J Med Chem, 2002; 45(17): 3692-3702.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.
Campbell et al., "Folate-binding protein is a marker for ovarian cancer," *Cancer Res.*, 1991; 51: 5329-5338.
Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid—polylysine-mediated introduction of c-myb antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
DeVita, Jr., Vincent et al (eds); *Biologic Therapy of Cancer*; 2nd ed., J.B. Lippincott Company; 1995.
Domling A. et al., "Myxobacterial Epothilones and Tubulysins as Promising Anticancer Agents," *Molecular Diversity*, 2005; 9: 141-147.

Douglas J.T. et al., "Targeted Gene Delivery by Tropism-Modified Adenoviral Vectors," *Nat. Biotechnol.*, 1996, vol. 14, pp. 1574-1578.
U.S. Appl. No. 60/946,092, filed Jun. 25, 2007, Vlahov et al.
Eichman, J.D. et al., "The Use of PAMAM Dendrimers in The Efficient Transfer of Genetic Material Into Cells", Jul. 2000, *PSTT*, vol. 3, No. 7, pp. 232-245.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
Foong, Louise Y. et al.; "Development of a Novel Thiol Reagent for Probing Ion Channel Structure: Studies in a Model System," Biochemistry, 1997, vol. 36, pp. 1343-1348.
Greene T.E. et al., "Protective Groups in Organic Synthesis," 2d edition, John Wiley & Sons, Inc. New York (1991).
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.
Hofland et al., "Folate-targeted gene transfer in vivo," *Mol Ther* 5(6): 739-744 (2002).
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Holladay et al., "Riboflavin-mediated delivery of a macromolecule into cultured human cells," *Biochim Biophys Acta*, 1426(1): 195-204 (1999).
U.S. Appl. No. 60/982,595, filed Oct. 25, 2007, Vlahov et al.
U.S. Appl. No. 60/036,176, filed Mar. 13, 2008, Vlahov et al.
U.S. Appl. No. 61/036,186, filed Mar. 13, 2008, Vlahov et al.
U.S. Appl. No. 12/739,579, filed Apr. 23, 2010, Vlahov et al.
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.

(56) References Cited

OTHER PUBLICATIONS

Jones T.R. et al., "A potent antitumour quinazoline inhibitor of thymidylate synthetase: synthesis, biological properties and therapeutic results in mice," *Eur, J Cancer*, 1981; 17(1):11-9.

Jones T.R. et al., "Quinazoline antifolates inhibiting thymidylate synthase: variation of the amino acid," *J Med Chem*, 1986; 29(6):1114-8.

U.S. Appl. No. 12/775,824, filed May 7, 2010, Green et al.

U.S. Appl. No. 12/666,712, filed Dec. 24, 2009, Leamon et al.

Jung K.H. et al., "Intramolecular o-glycoside bond formation," *Chem. Rev.*, 2000, 100, 4423-42.

Kagechika H et al., "Synthetic Retinoids: Recent Developments Concerning Structure and Clinical Utility," *Journal of Medicinal Chemistry*, 2005; vol. 48, No. 19, pp. 5875-5883.

Kamen et al., "Delivery of folates to the cytoplasm fo MA 104 cells is mediated by a surface receptor that recycles," *J. Biol. Chem.*, 263: 13602-13609 (1988).

Kamen et al., "The folate receptor works in tandem with a probenecid-sensitive carrier in MA 104 cells in vitro,"*J. Clin. Invest.*, 87(4): 1442-1449 (1991).

Kamen, B. A. et al., "Receptor-mediated folate accumulation is regulated by the cellular folate content," *Proc. Natl. Acad Sci. USA*, 83: 5983-5987 (1986).

Kandiko C.T. et al., "Inhibition of Rat Brain Pyruvate Dehydrogenase by Thiamine Analogs," *Biochemical Pharmacology*, 1988; vol. 37, No. 22, pp. 4375-4380.

Kane et al., "The influence of extracellular folate concentration on methotrexate uptake by human KB cells. Partial characterization of a membrane-associated methotrexate binding protein," *J. Biol. Chem.*, 261: 44-49 (1986).

Kim et al., "Synthesis and biological activity of 10-thia-10-deaza analogs of folic acid, pteroic acid, and related compounds", *Journal of Medical Chemistry*, 18: 776-780 (1975).

Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.

Kumar H.P. et al., "Folate transport in *Lactobacillus salivarius*. Characterization of the transport mechanism and purification and properties of the binding component," *J. Biol. Chem..* 1987; 262(15):7171-7179.

Ladino et al., "Folate-maytansinoids: target-selective drugs of low molecular weight," *Int. J. Cancer*, 73(6): 859 864 (1997).

Lambooy J. P., "Riboflavin Analogs Utilized for Metabolism by a *Lactobacillus casei* Mutant," *Int. J. Biochem.*, vol. 16, No. 2, 1984, pp. 231-234.

Landuer W. et al., "The Interaction in Teratogenic Activity of the Two Niacin Analogs 3-acetylpyridine and 6-aminonicotinamide,"*J Exp Zool*, 151(3):253-258 (1962).

Langone, J.J., et al., "Radioimmunoassays for The Vinca Alkaloids, Vinblastine and Vincristine", 1979, *Analytical Biochemistry*, No. 95, pp. 214-221.

Larock R.C., "Comprehensive Organic Transformations, a guide to functional group preparations," VCH Publishers, Inc. New York (1989).

Leamon CP et al, "Cytotoxicity of folate-*Pseudomonas* exotoxin conjugates toward tumor cells. Contribution of translocation domain," *J. Biol. Chem.* 268(33): 24847-24854 (1993).

Leamon CP et al., "Comparative Preclinical Activity of the Folate-targeted Vinca Alkaloid Conjugates EC140 and EC145," *Int J Cancer*, 2007; 121(7):1585-92.

Leamon CP et al., "Cytotoxicity of momordin-folate conjugates in cultured human cells," *J. Biol. Chem.*, 1992; 267(35): 24966-24971.

Leamon CP et al., "Delivery of macromolecules into living cells: a method that exploits folate receptor endocytosis," *Proc. Natl. Acad. Sci. USA* 88(13): 5572-5573 (1991).

Leamon CP et al., "Folate-mediated targeting: from diagnostics to drug and gene delivery," *Drug Discovery Today* 6: 36-43 (2001).

Leamon CP et al., "Folate-targeted chemotherapy," *Adv Drug Deliv Rev*, 2004;56(8): 1127-41.

Leamon CP et al., "Membrane folate-binding proteins are responsible for folate-protein conjugate endocytosis into cultured cells," *Biochem. J.* 291: 855-860 (1993).

Leamon CP et al., "Selective targeting of malignant cells with cytotoxin-folate conjugates," *J. Drug Target.* 2(2): 101-112 (1994).

Leamon CP et al., "Synthesis and biological evaluation of EC140: a novel folate-targeted vinca alkaloid conjugate," *Bioconjug Chem*, 2006;17(5):1226-32.

U.S. Appl. No. 60/590,580, filed Jul. 23, 2004, Vlahov et al.

Leamon CP et al., "Synthesis and Biological Evaluation of EC20: A New Folate-Derived, (99m)Tc-Based Radiopharmaceutical," *Bioconjug. Chem.* 13(6): 1200-1210 (2002).

Leamon CP et al., "Synthesis and biological evaluation of EC72: a new folate-targeted chemotherapeutic," *Bioconjug Chem.*, 2005;16(4):803-11.

Leamon et al., "Folate-mediated drug delivery: effect of alternative conjugation chemistry," *J. Drug Target* 7(3): 157-169 (1999).

Lee et al, "Measurement of Endosome pH Following Folate Receptor-Mediated Endocytosis," *Biochim. Biophys. Acta* 1312(3): 237-242 (1996).

Lee W.W. et al., "Folic acid antagonists. Methotrexate analogs containing spurious amino acids. Dichlorohomofolic acid," *Journal of Medical Chemistry*, 17: 326-330 (1974).

Lee et al., "Synthesis and evaluation of taxol-folic acid conjugates as targeted antineoplastics," *Bioorg Med Chem.* 10(7): 2397-2414, (2002).

Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.

Lee, R. J. And Huang, L., "Folate-Targeted, Anionic Liposome-Entrapped Polylysine-Condensed Dna for Tumor Cell-Specific Gene Transfer," *J. Biol. Chem.* 271(14): 8481-8487 (1996).

Lee, R. J. and Low, P. S, "Delivery of liposomes into cultured KB cells via folate receptor-mediated endocytosis," *J. Biol. Chem.* 269(5): 3198-3204 (1994).

Lee, R. J. and Low, P. S., "Folate-mediated tumor cell targeting of liposome-entrapped doxorubicin in vitro," *Biochim. Biophys. Acta* 1233: 134-144 (1995).

Lemon, Julia, et al., "Conversion of Pterolyglutamic Acid to Pteroic Acid by Bacterial Degradation," *Archives of Biochemistry*, 1948; vol. 19, pp: 311-316.

Levy, Carl C., et al. "The Enzymatic Hydrolysis of Methotrexate and Folic Acid", 1967, *The Journal of Biological Chemistry*, vol. 242, No. 12, pp: 2933-2938.

Lewis et al., "Receptor-mediated folate uptake is positively regulated by disruption of actin cytoskeleton," *Cancer Res.* 58(14): 2952-2956 (1998).

Li et al, "Targeted delivery of antisense oligodeoxynucleotides by LPDII," *J. Liposome Res.* 7(1): 63 (1997).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).

Lonsdale D, "A Review of the Biochemistry, Metabolism and Clinical Benefits of Thiamin(e) and Its Derivatives," publication, Advance Access Publication, vol. 3, Feb. 2006, pp. 49-59.

Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-238.

Lu et al., "Folate-targeted enzyme prodrug cancer therapy utilizing penicillin-V amidase and a doxorubicin prodrug," *J. Drug Target*, 7(1): 43-53 (1999).

Lu, J. Y. and Low, P. S., "Folate targeting of haptens to cancer cell surfaces mediates immunotherapy of syngeneic murine tumors," *Cancer Immunol Immunother*, 51: 153-162 (2002).

Lu, J.Y. and Low, P. S., "Folate-mediated delivery of macromolecular anticancer therapeutic agents," *Adv. Drug Del Rev*, 2002; 54(5): 675-693.

(56) References Cited

OTHER PUBLICATIONS

Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).

Mack D.O. et al., "The Carboxylation Activity of Vitamin K Analogs with Substitutions at Position 2, 3, or 5," *Journal of Biological Chemistry*, 1979; vol. 254, pp. 2656-2664.

Mancuso A.J. et al., "Activated Dimethyl Sulfoxide: Useful Reagents for Synthesis," *Synthesis*, 1981, pp. 165-184.

March, Advanced Organic Chemistry, 1992, John Wiley & Sons, 4th Ed., pp. 362-363, 816, 885, 896.

Mathais et al., "Receptor-mediated targeting of 67Ga-deferoxamine-folate to folate-receptor-positive human KB tumor xenografts," *Nucl Med Biol*, 26(1): 23-25 (1999).

Mathais et al., "Synthesis of [(99m)Tc]DTPA-folate and its evaluation as a folate-receptor-targeted radiopharmaceutical," *Bioconjug Chem*, 11(2): 253-257 (2000).

Mathias et al., "Indium-111-DTPA-Folate as a potential folate-receptor-targeted radiopharmaceutical," *J. Nucl. Med.*, 39(9): 1579-1585 (1998).

Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).

Mathias, C. J., "A kit formulation for preparation of [(111)In]In-DTPA-folate, a folate-receptor-targeted radiopharmaceutical," *Nucl. Med. Biol.*, 25(6): 585-587 (1998).

Matsui et al., "Studies on mitomycins. III. The synthesis and properties of mitomycin derivatives," *J Antibiot*, 21: 189-198 (1968).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

McAlinden TP et al., "Synthesis and Biological Evaluation of a Fluorescent Analogue of Folic Acid," *Biochemistry*, 1991; 30: 5674-81.

McHugh M et al., "Demonstration of a High Affinity Folate Binder in Human Cell Membranes and Its Characterization in Cultured Human KB Cells,"*J Biol Chem*, 1979; 254(22):11312-8.

Melani et al., "Targeting of interleukin 2 to human ovarian carcinoma by fusion with a single-chain Fv of antifolate receptor antibody," *Cancer Res.* 58(18): 4146-4154 (1998).

Melby, E.L. et al, "Entry of Protein Toxins in Polarized Epithelial Cells"; *Cancer Research*, 1993; 53: 1755-1760.

Mislick et al., "Transfection of folate-polylysine DNA complexes: evidence for lysosomal delivery," *Bioconjug. Chem.*, 6(5): 512-515 (1995).

Mock D.M. et al., "Urinary Biotin Analogs Increase in Humans During Chronic Supplementation: the Analogs are Biotin Metabolites," *Am J Physiol Endocrinol Metab*, 1997; 272: E83-E85.

Morshed et al., "Folate transport proteins mediate the bidirectional transport of 5-methyltetrahydrofolate in cultured human proximal tubule cells," *J. Nutr.*, 127(6): 1137-1147 (1997).

Nair et al., "Folate analogs altered in the C9-N10 bridge region. 14. 11-Oxahomofolic acid, a potential antitumor agent", *Journal of Medical Chemistry*, 23: 59-65 (1980).

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry*, 22: 850-855 (1979).

Nair et al., "Folate analogs. 20. Synthesis and antifolate activity of 1',2',3',4',5',6'-hexahydrohomofolic acid,"*Journal of Medical Chemistry*, 26: 135-140 (1983).

Nair et al., "Folate analogs. 21. Synthesis and antifolate and antitumor activities of N10-(cyanomethyl)-5,8-dideazafolic acid," *Journal of Medical Chemistry*, 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9-N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nimmo-Smirth R.H. et al., "Some Effects of 2-deaminopteroylglutamic Acid upon Bacterial Growth," *J. Gen. Microbial.*, 1953; 9: 536-544.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nomura, Makoto et al., "Development of an Efficient Intermediate α[2-(Trimethylsilyl)ethoxy]-2-*N*-[2-(trimethylsilyl)ethoxycarbonyl]folic Acid, for the Synthesis of Folate (γ)-Conjugates, and Its Application to the Synthesis of Folate-Nucleoside Congugates,"*Journal of Organic Chemistry*, 2000, vol. 65, pp. 5016-5021.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Olsnes S. et al., "Immunotoxins-entry into cells and mechanisms of action," *Immunology Today*, 1989; vol. 10, No. 9, pp. 291-295.

Patrick et al., "Folate Receptors As Potential Therapeutic Targets in Choroid Plexus Tumors of Sv40 Transgenic Mice," *J. Neurooncol,.* 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc.*, No. 128, pp. 16018-16019.

Pizzorno G., et al., "Intracellular metabolism of 5,10-dideazatetrahydrofolic acid in human leukemia cell lines,"*Molecular Pharmacology*, 1991, 39 (1), pp. 85-89.

Plante et al., "Polyglutamyl and polylysyl derivatives of the lysine analogues of folic acid and homofolic acid," *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prabhu V. et al., "*Arabidopsis* dihydropteroate synthase: general properties and inhibition by reaction product and sulfonamides," *Phytochem.*, 1997; 45(1): 23-27.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.

Punj, V. et al., "Effect of Vitamin D Analog (1α Hydroxy D5) Immunoconjugated to Her-2 Antibody on Breast Cancer," *Int. J. Cancer*, 2004; 108: 922-929.

Raghavan B et al., "Cytotoxic Simplified Tubulysin Analogues," *J. Med. Chem.*, 2008; 51(6), pp. 1530-1533.

(56) References Cited

OTHER PUBLICATIONS

Reddy et al., "Optimization of folate-conjugated liposomal vectors for folate receptor-mediated gene therapy," *J. Pharm. Sci*, 88(11): 1112-1118 (1999).

Reddy et al., "Preclinical evaluation of EC145, a folate-vinca alkaloid conjugate," *Cancer Res.*, 2007; 67:4434-42.

Reddy et al., "Retargeting of viral vectors to the folate receptor endocytic pathway," *J Control Release*, 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.

Remington: The Science & Practice of Pharmacy, 21th Edition (Lippincott Williams & Wilkins, 2005).

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

Rijnboutt et al., "Endocytosis of GPI-linked membrane folate receptor-alpha," *J. Cell Biol.*, 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*, 15: 1310-1312 (1972).

Roberts et al., "Folic acid analogs. Modifications in the benzene-ring region. 1. 2'- and 3'-Azafolic acids," *Journal of Medical Chemistry*, 14: 125-130 (1971).

Roberts et al., "Folic acid analogs. Modifications in the benzene-ring region. 4. 3'-Ethyl- and 3'-isopropylfolic acids," *Journal of Medical Chemistry*, 17: 219-222 (1974).

Rose W.C., "Taxol-Based Combination Chemotherapy and Other In Vivo Preclinical Antitumor Studies," *J Natl Cancer Inst Monogr*, 1993, No. 15, pp. 47-53.

Ross et al., "Differential regulation of folate receptor isoforms in normal and malignant tissues in vivo and in established cell lines. Physiologic and clinical implications," *Cancer*, 73(9): 2432-2443, (1994).

Ranasinghe, M. G. et al.; "A Facile Synthesis of Unsymmetrical Thiolsulfonates via Sulfonylation of Mercaptans," *Synthetic Communications*, 1998, 18(3), pp. 227-232.

Rothberg et al, "Cholesterol controls the clustering of the glycophospholipid-anchored membrane receptor for 5-methyltetrahydrofolate," *J. Cell Biol.*, 111(6): 2931-2938 (1990).

Rothberg et al., "The glycophospholipid-linked folate receptor internalizes folate without entering the clathrin-coated pit endocytic pathway," *J. Cell Biol.*, 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," *J. Biol. Chem.*, 1989; 264: 5806-5811.

Sargent D.R. et al., "Antimetabolites of Pantothenic Acid, Ureido— and Carbamoyl-Derivatives," *Texas Reports on Biology and Medicine*, 1975, vol. 33, No. 3, pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.

Scott J.M, "Preparation and Purification of Pteroic Acid from Pteroylglutamic Acid (Folic Acid)," *Methods in Enzymology*, 1980, vol. 66, pp. 657-660.

Search Report for Taiwan Patent Application No. 093101735, dated Jul. 14, 2007, 1 page.

Senter, Peter D. et al.; "Development of a Drug-Release Strategy Based on the Reductive Fragmentation of Benzyl Carbamate Disulfides," *J. Org. Chem.*, 1990, vol. 55, pp. 2975-2978.

Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.

Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.

Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.

Shoup T.M. et al., "Synthesis of Fluorine-18-Labeled Biotin Derivatives: Biodistribution and Infection Localization," *J. Nucl. Med.*, 1994; 35: 1685-1690.

Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.

Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits *Plasmodium falciparum* Pantothenate Kinase and Represses the Proliferation of Malaria parasites," *Antimicrobial Agents and Chemotherapy*, 2005; 49(11): 4649-4657.

Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.

Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.

Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.

Temple et al., "Synthesis of pseudo cofactor analogs as potential inhibitors of the folate enzymes," *Journal of Medical Chemistry*, 25: 161-166 (1982).

Theti, D. S. et al., "Selective delivery of CB300638, a cyclopentalglquinazoline-based thymidylate synthase inhibitor into human tumor cell lines overexpressing the alpha-isoform of the folate receptor," *Cancer Res*, 2003; 63(13): 3612-3618.

Toffoli et al., "Overexpression of folate binding protein in ovarian cancers," *Int. J. Cancer* 74(2): 193-198 (1997).

Toraya T. et al., "Immobilized Derivatives of Vitamin B12 Coenzyme and Its Analogs," *Methods in Enzymology*, vol. 67, pp. 57-66.

Takeda, Kazuyoshi et al.; "A Synthesis of a New Type of Alkoxycarbonylating Reagents from 1,1-Bis[6-(trifluoromethyl)benzotriazolyl] Carbonate (BTBC) and Their Reactions," *Synthesis*, Jun. 1987, pp. 557-560 and 1191.

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.

Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of TRAIL for its receptors. DR5 is the highest affinity receptor," *J Biol Chem*, 2000; 275(30):23319-25.

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).

(56) References Cited

OTHER PUBLICATIONS

Ueda M. et al., "Effect of Vitamin B12 Derivatives on Urinary Excretion of Methylmalonic Acid in Liver Diseases," *Acta Med Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Weinstock et al., "Folic acid analogs. II. p-{[(2,6-Diamino-8-purinyl)methyl]aminol}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate binding protein (mFBP) in human CCRF-CEM leukemia cells," *Procceedings of the American Association for Cancer Research*, 1991; 32:328.
Wiener et al., "Targeting dendrimer-chelates to tumors and tumor cells expressing the high-affinity folate receptor," *Invest. Radiol.* 32(12): 748-54 (1997).
Wu M. et al., "Clustering of GPI-anchored folate receptor independent of both cross-linking and association with caveolin," *J. Membr. Biol.* 159(2): 137-147 (1997).
Zimmer H. et al., "Potential anticancer agents V., Synthesis of folic acid and pteroic acid analogs derived of caffeine and theophylline," *Arzneimittelforschung*, 1966, 16(4), pp. 541-545.
Zimmerman, J., "Folic acid transport in organ-cultured mucosa of human intestine. Evidence for distinct carriers," *Gastroenterol.* 99(4): 964-972 (1990).
Angier, R. B., et al., "Pteroic Acid Analogs Containing Arsenic," J. American Chem. Soc., vol. 76, 1954, pp. 902-904.
Boothe, J. H., et al., "Pteroic Acid Derivatives. II. Pteroyl-γ-glutamylglutamic Acid and Pteroyl-γ-glutamyly-γ-glutamylglutamic Acid," J. American Chem. Soc., vol. 70, 1948, pp. 1099-1102.
Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).
Wikipedia, Derivative (Chemistry), http://en.wikipedia.org/wiki/Derivative_(chemistry), downloaded Dec. 16, 2009.
Wikipedia, Analog (Chemistry), http://en.wikipedia.org/wiki/Analog_(chemistry), downloaded Dec. 16, 2009.
Wikipedia, List of Purification Methods in Chemistry, http://en.wikipedia.org/wiki/List_of_purification_methods_in_chemistry, downloaded Dec. 16, 2009.
Wikipedia, Solution, http://en.wikipedia.org/wiki/Solution, downloaded Dec. 17, 2009.
Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.
Wikipedia, Conjugate, http://en.wikipedia.org/wiki/Conjugate, downloaded Dec. 17, 2009.
Wikipedia, Complex (Chemistry), http://en.wikipedia.org/wiki/Complex_(chemistry), downloaded Dec. 23, 2009.
International Search Report for PCT/US2005/026068, dated Nov. 21, 2005.
Leamon Christopher P., "Aspects of Folate-Mediated Drug Delivery . . . Beyond Purdue" PowerPoint Presentation presented at Purdue University on May 4, 1999, (22 pages).
Achilefu et al. "A New Method for the Synthesis of Tri-tert-butyl Diethylenetriaminepentaacetic Acid Its Derivatives" *J. Org. Chem.* 2000;65:1562-1565.
Carl et al. "A novel connector linkage applicable in prodrug design" J. Med. Chem. 1981;24(5):479-480.
Coney et al. "Cloning of a tumor-associated antigen: MOv18 and MOv19 antibodies recognize a folate-binding protein" Cancer Res. 1991;51(22):6125-32.
Crapatureanu et al. "Molecular necklaces. Cross-linking hemoglobin with reagents containing covalently attached ligands" Bioconjugate Chemistry, 1999;10(6):1058-67.
Darnell, Ed. Molecular Cell Biology W. H. Freeman, San Francisco 1990;326-333.
DeNardo, Gerald. "When is Too Much Too Much and Yet Not Enough? Alas, a Plethora of Opportunities but Where's the Beef?" J. of Nuclear Medicine 2000; 41(3):470-3.
Dorwald, F. Z., "Side Reactions in Organic Synthesis: A Guide to Successful Synthesis Design," Wiley-VCH, Weinheim, 2005, p. ix of preface.
Forgac. "Structure and function of vacuolar class of ATP-driven pumps" Physiological Rev. 1989; 69(3): 765-795.
Garrett et al. "Synthesis and characterisation of polyamine-poly(ethylene glycol) constructs for DNA binding and gene delivery" Bioorganic & Medicinal Chemistry, 2000; 8(7):1779-1797.
Henderson et al. "Mediated uptake of folate by a high-affinity binding protein in sublines of L1210 cells adapted to nanomolar concentrations of folate" J. Membrane Biol., 1988;101:247-258.
Huang et al. "Design, syntheses and sequence selective DNA cleavage of functional models of bleomycin-II. 1,2-trans-di substituted cyclopropane units as novel linkers" Bioorganic & Medicinal Chemistry, 1995;3(6):647-57.
Jansen et al., "Identification of a Membrane-Associated Folate-Binding Protein in Human Leukemic CCRF-CEM Cells with Transport-Related Methotrexate Resistance" in Cancer Res., 1989, 49, 2455-2459.
Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.
Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

(56) References Cited

OTHER PUBLICATIONS

Kamen et al., 1986, "Receptor-mediated folate accumulation is regulated by cellular folate content" Proc. Natl. Acad. Sci., U.S.A. 83, 5983-5987.
Ke et al. "Targeting the Tumor-Associated Folate Receptor with a 111-IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.
Kemp et al. "New Protective Groups for Peptide Synthesis-I The Bic Group Base and Solvent Lability of the 5-B enzi soxazolymethyl eneoxycarbonyl amino function" Tet. Lett. 1975;52:4625-4628.
Kutsky RJ. Handbook of Vitamins, Minerals, and Hormones, 2nd Edition. New York: Van Nostrand Reinhold: 1981;263-277.
Lee et al. "Prolonged circulating lives of single-chain Fv proteins conjugated with polyethylene glycol: a comparison of conjugation chemistries and compounds" Bioconjugate Chemistry, 1999;10(6):973-81.
Li et al. "Local concentration of folate binding protein GP38 in sections of human ovarian carcinoma by concentration of in vitro quantitative autoradiography." J. Nucl. Med. 1996; 37:665-672.
Linder et al., In vitro & in vivo studies with a-and y-isomers of 99'Tc-oxa folate show uptake of both isomers in folate receptor (+) KB Cell Lines J. Nuclear Med. 2000;41(5):470 Suppl.
Mehvar R "Dextrans for targeted and sustained delivery of therapeutic and imaging agents" [Review] Journal of Controlled Release, 2000;69(1):1-25.
Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.
Miotti et al., "Characterization of Human Ovarian Carcinoma-Associated Antigens Defined by Novel Monoclonal Antibodies with Tumor—Restricted Specificity" Int. J. Cancer, 1987;39:297-303.
Pastan et al, eds. "The Pathways of Endocytosis" Endocytosis, Plenum Press, New York 1985;1-40.
Peterson et al. "Enzymatic cleavage of peptide-linked radiolabels from immunoconjugates" Bioconjugate Chemistry, 1999;10(4):553-7.
Pizzorno et al. "5,10-Dideazatetrahydrofolic acid (DDATHF) transport in CCRFCEM and MA104 cell lines." J. Biol, Chem., 1993; 268(2):247-258.
Rothenberg et al. "Further observations on the folate-binding factor in some leukemic cells" J. Clin. Invest. 1971; 50(3):719-726.
Selhub et al. "The folate binding protein of rat kidney. Purification, properties, and cellular distribution" J. Biol. Chem. 1984;259(10):6601-6606.
Selhub et al. "Renal folate adsorption and the kidney folate binding protein I. Urinary Clearance studies" Am. J Physiol. 252:F750-F756.
Selhub et al. "Renal folate adsorption and the kidney folate binding protein II. Microinfusion studies" Am. J. Physiol. 252:F757-F760.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.
Toffoli et al. "Expression of folate binding protein as a prognostic factor for response to platinum-containing chemotherapy and survival in human ovarian cancer" Int. J. Cancer (Pred. Oncol) 1998; 79:121-126.

Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; Int. Journal Cancer; Vo. 119; pp. 757-764.
Brown, Nicole E., et al., "Delayed Cystogenesis and Increased Ciliogenesis Associated with th Re-Expression of Polaris in Tg737 Mutant Mice", 2003, Kidney International, vol. 63, pp. 1220-1229.
Bukanov Nikolay, O. et al., "Long-Lasting Arrest of Murine Polycystic Kidney Disease With CDK Inhibitor Roscovitine", Dec. 14, 2006; Nature; vol. 444; pp. 949-952.
Hay, Nissim, et al., "Upstream and Downstream of mTOR", 2004, Genes & Development, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp: 714-719.
Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.
Nauta, Jeroen, et al., "Renal and Biliary Abnormalities in a New Murine Model of Autosomal Recessive Polycystic Kidney Disease", 1993, Pediatr. Nephrol. No. 7, pp. 163-172.
Piontek, Klaus B., et al. "A Functional Floxed Allele of Pkd1 that Can Be Conditionally Inactivated In Vivo", J. Am. Soc. Nephrol. vol. 15, pp. 3035-3043.
Shillingford, Jonathan M., et al., "The mTOR Pathway is Regulated by Polycystin-1, and its Inhibition Reverses Renal Cystogenesis in Polycyctic Kidney Disease", Apr. 4, 2006, PNAS. vol. 103, No. 14, pp. 5466-5471.
Ke Cy et al., "Folate-Receptor-Targeting of In-111 Using Pteroic Acid Conjugates of Benzyl-DTPA and Benzyl-DOTA," J. Nucl. Med., 2004; 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery," Molecular Pharmacology, 2004; 66:1406-1414.

(56) References Cited

OTHER PUBLICATIONS

Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Functional analog, http://en.wikipedia.org/wiki/Functional_analog, downloaded Apr. 7, 2009.
Wikipedia, Folic acid, http://en.wikipedia.org/wiki/Folic_acid, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Weitman et al. "Distribution of the folate receptor GP38 in normal and malignant cell lines and tissues" Cancer Res. 1992;52(12):3396-3401.
Atkinson SF et al., "Conjugation of folate via gelonin carbohydrate residues retains ribosomal-inactivating properties of the toxin and permits targeting to folate receptor positive cells." Journal of Biological Chemistry, 2001, 276(30), pp. 27930-27935.
Matulic-Adamic J et al., "An efficient synthesis of the ribozyme-folate conjugate," Tetrahedron Letters, 2002; 43(25):4439-4441.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:—"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake," Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).
Dube D et al., "Preparation and Tumor Cell Uptake of Poly(N-isopropylacrylamide) Folate Conjugates"; Bioconjugate Chem, 2002; 13: 685-692.
Evans et al., "Synthessis of biotin conjugates of the antifungal compound cymoxanil," Pest Manag Sci, 2002; 58: 392-396.
Rao et al., Journal of Medicinal Chemistry, 1985, 28:1079-1088.
Conrad et al, Journal of Medicinal Chemistry, 1979, 22(4): 391-400.
Wang et al., "Structure-activity and high-content imaging analyses for novel tubulysins," Chemical Biology & Drug Design. 2007: 70(21: 75-86.
Patterson et al., "Design, synthesis, and biological properties of highly potent tubulysin D analogues," Chemistry—A European Journal, 2007: 13(34): 9534-9541.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.
Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002.
Putnam et al., "Polymer conjugates with anticancer activity", Advances in Polymer Science 1995, 122, 55-123.

Umemoto et al., "Molecular design of methotrexate-antibody conjugates for targeted cancer treatment", Journal of Bioactive and Compatible Polymers. 1992, 7(2), 191-219.
Sanderson et al., "In vivo drug-linker stability of an anti-CD30 dipeptide-linked auristatin immunoconjugate," Clinical Cancer Research, 2005: 11:-843-852.
Wu et al., "Enhancing the enantioselectivity of candida lipase catalyzed ester hydrolysis via noncovalent enzyme modification," Journal of American Chemical Society, 1990: 112:1990-1995.
Patterson et al., "Expedient synthesis of N-Methyl tubulysin analogues with high cytotoxicity," Journal of Organic Chemistry, 2008: 73:4365-4369.
Gabizon et al., Clin Cancer Res 9:6551-59 (2003).
Pouvreau, Isabelle et al.: "Effect of macrophage depletion by liposomes containing dichloromethylene-diphosphonate on endotoxin induce uveitis." J. Neuroimmun. (1998)86 p. 171-181.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.
Definition of derivative and analog, from http://cancerweb.ncl.ac.uk/cgi-omd?query=derivative and http://cancerweb.ncl.ac.uk/cgi-bin/omd?query=analog, pp. 1-5, accessed Jul. 7, 2005.
Kaneko, Takushi, "New Hydrazone Derivatives of Adiramycin and their Immunoconjugates—A Correlation between Acid Stability and Cytotoxicity", Bioconj. Chem., vol. 2. No. 3. pp. 131-141 (May 1, 1991).
PCT International Search Report/Written Opinion for PCT/US2009/061049, completed Mar. 15, 2010.
Polyak et al., "Introduction of spacer peptides N-terminal to a cleavage recognition motif in recombinant fusion proteins can improve site-specific cleavage," Protein Eng., 1997: 10(6)-615-9.
Univesity of Maryland Medical Center (UMMC), Vitamin B9 (folic acid), 2014, http://umm.edu/health/medical/altmed/supplement/vitamin-b9-folic-acid, pp. 1-8.
Cerner Multum, Inc., Drugs.com, Folic Acid, http://www.drugs.com/folic_acid.html?printable=1, 1996-2014, Version: 5.01, Revision Date Oct. 15, 2009, pp. 104.
PCT International Search Report/Written Opinion prepared for PCT/US2010/061897, mailed Mar. 11, 2011.
Water, from http://www.biology-ionline.org/dictionary/Water, pp. 103, accessed Apr. 24, 2014.
Niosh List of antineoplastic and Other Hazardous Drugs in Healthcare settings 2010, pp. 1-16, published Sep. 20, 2010.
Chae et al, Recombinant Expression, Isotope labeling and purification of the Vitamin D Receptor Binding Peptide, Bull. Korean Chem Soc. 2011, 32, pp. 4337-4340.
Rudinger, peptide Hormones, JA Parsons, Ed., 1976, pp. 1-7.
SIGMA, 2004, pp. 1-2.
Berendsen, A Glimpse of the Holy Grail?, Science, 1998, 282, pp. 642-643.
Voet et al, Biochemistry, John Wiley & Sons Inc., 1995, pp. 235-241.
Ngo et al, Computational Complexity, Protein Structure protection, and the Levinthal Paradox, 1994, pp. 491-497.
Bradley et al, Limits of Cooperativity in a Structurally Modular Protein: Response of the Notch Ankyrin Domain to Analogous Alanine Substitutions in Each Repeat, J. Mol. Biol, 2002, 324, pp. 373-386.
Definition of moiety, from http://dictionary.reference.com/browse/moiety, pp. 1-3, accessed Aug. 26, 2010.
Muller, Prodrug approaches for Enhancing the Bioavailability of Drugs with Low Solubility, Chemistry & Biodiversity, 2009, 6, pp. 2071-2083.
Beaumont et al, Design of ester prodrugs to enhance oral absorption of poorly permeable compounds: Challenges to the Discovery Scientist, Current Drug Metholism, 2003, 4, 461-485.
Hyo-Kyung Han, Targeted prodrug design to optimize drug delivery, AAPS Pharmsci 2000, 2(10), article 6, p. 1-11.

(56) References Cited

OTHER PUBLICATIONS

Yashveer Singh et al, Recent trends in targeted anticancer prodrug and conjugate design, Curr Med Chem, 2008, 15(18): 1802-1826.
Testa B, Prodrug Research: Futile or Fertile?, Biochem Pharm, 2004, 68, pp. 2097-2106.
Ettmayer et al, Lessons learned from marketed and investigational prodrugs, J. Med Chem, 2004, 47(10), pp. 2393-2404.
Machine Translation of WO 2004/005326, Jan. 15, 2004, pp. 1-5.
European Search Report prepared for corresponding European Application Serial No. 08841521.1, mailed Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
PCT International Search Report/Written Opinion for PCT/US2008/056824, completed Jul. 24, 2009.

* cited by examiner

BIVALENT LINKERS AND CONJUGATES THEREOF

CROSS REFERENCE TO RELATED APPLICATIONS

This application is a Continuation Application of U.S. patent application Ser. No. 11/632,895 filed Jan. 19, 2007, now U.S. Pat. No. 8,288,557, issued Oct. 16, 2012, which is a U.S. national application under 37 C.F.R. §371(b) of PCT international application No. PCT/US2005/026068 filed Jul. 22, 2005, which claims the priority benefit under 35 U.S.C. §119(e) of U.S. provisional patent application No. 60/590,580, filed Jul. 23, 2004, the disclosures of each of which are incorporated by reference herein in their entireties.

FIELD OF THE INVENTION

This invention pertains to bivalent linkers, and the synthesis and use thereof. In particular, this invention pertains to the synthesis and use of bivalent linkers in preparing vitamin, drug, diagnostic agent, and/or imaging agent conjugates.

BACKGROUND

Drug, vitamin, diagnostic, and imaging agent conjugates have been used to treat, diagnose, and evaluate various disease states in humans and in animals.

In many cases these drug, vitamin, diagnostic, and imaging agent conjugates include intervening linkers separating for example a targeting ligand from a drug, diagnostic agent, or imaging agent. These linkers include a wide variety of bivalent fragments that may be used separately or when linked together for inclusion in conjugates to for example space a drug, diagnostic agent, or imaging apart from other parts of the conjugate, such as for example a vitamin or other targeting ligand. These linkers may also be stable to the metabolic, physiological, or biological conditions present when they are administered to humans and animals, or alternatively these linkers may undergo various routes of cleavage and/or fragmentation under such conditions. There exists a continuing need for bivalent linkers that can be generally used in drug, vitamin, diagnostic, and imaging agent conjugates.

SUMMARY OF THE INVENTION

Illustratively, the present invention includes divalent linkers, which are alternatively referred to as bivalent linkers, that may be used to couple, link, bond, attach, or otherwise associate two or more chemical entities. This coupling, linking, attachment, or association may be used in the formation of conjugates of such chemical entities. Those chemical entities include targeting ligands and receptor-binding ligands, such as vitamins. Those chemical entities also include drugs for treating various diseases or disease states, and imaging and diagnostic agents for diagnosing, detecting, or otherwise monitoring various diseases or disease states.

In one embodiment, one chemical entity includes a vitamin receptor-binding moiety, and another entity includes a drug, imaging agent, diagnostic agent, another bivalent linker, or another bivalent linker conjugated with a drug, imaging agent, diagnostic agent. It is appreciated that multiple linkers may be used between the two or more chemical entities to change the distance between the two entities and/or to change the physicochemical properties of the conjugates prepared therefrom.

In another embodiment, a compound is described that includes a first leaving group that is displaceable by a first nucleophile, a linker region, and a second leaving group that is displaceable by a second nucleophile, wherein the first nucleophile is a vitamin receptor-binding moiety, and the linker region comprises one or more bivalent linker units, which may be the same or different, and the second nucleophile is a drug, imaging agent, diagnostic agent, or another bivalent linker.

In another embodiment, a compound having the structure (V) is described

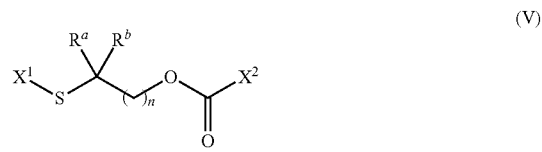

wherein n is an integer from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; and $X^1$ and $X^2$ are each independently selected leaving groups. In one aspect, each of the independently selected leaving groups $X^1$ and $X^2$ are displaceable by a nucleophile, such as a drug, a vitamin, an imaging agent, a diagnostic agent, or another bivalent linker nucleophile, and the like.

In another embodiment, a conjugate is formed from the compound of formula (V) by displacing one or more of the leaving groups $X^1$ and $X^2$ with a nucleophile, such as a drug, a vitamin, an imaging agent, a diagnostic agent, or another bivalent linker nucleophile, and the like.

In another embodiment, a compound having the structure (VI) is described

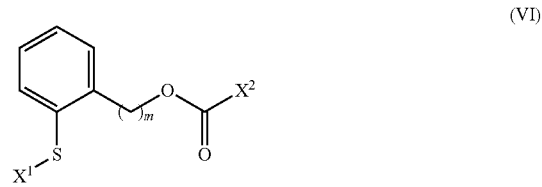

wherein m is an integer from 1 to about 4; and $X^1$ and $X^2$ are each independently selected leaving groups. In one aspect, each of the independently selected leaving groups $X^1$ and $X^2$ is displaceable by a nucleophile, such as a drug, a vitamin, an imaging agent, a diagnostic agent, or another bivalent linker nucleophile, and the like.

In another embodiment, a conjugate is formed from the compound of formula (VI) by displacing one or more of the leaving groups $X^1$ and $X^2$ with a nucleophile, such as a drug, a vitamin, an imaging agent, a diagnostic agent, or another bivalent linker nucleophile, and the like.

In another embodiment, a compound having the structure (VII) is described

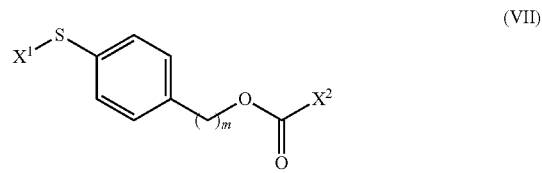

wherein m is an integer from 1 to about 4; and $X^1$ and $X^2$ are each independently selected leaving groups. In one aspect, each of the independently selected leaving groups $X^1$ and $X^2$ is displaceable by a nucleophile, such as a drug, a vitamin, an imaging agent, a diagnostic agent, or another bivalent linker nucleophile, and the like.

In another embodiment, a conjugate is formed from the compound of formula (VII) by displacing one or more of the leaving groups $X^1$ and $X^2$ with a nucleophile, such as a drug, a vitamin, an imaging agent, a diagnostic agent, or another bivalent linker nucleophile, and the like.

In one aspect, the conjugate has one of the following structures (VIII)

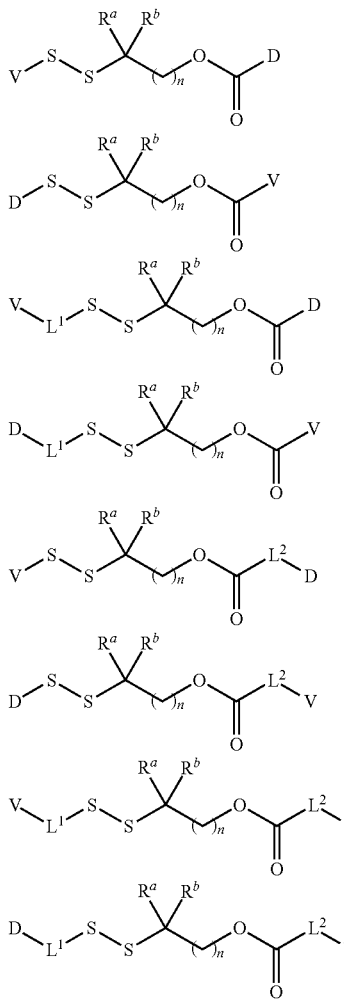

(VIII)

wherein n is an integer from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; $X^1$ and $X^2$ are each independently selected leaving groups; and $L^1$ and $L^2$ are each independently selected bivalent linkers.

In another embodiment, the conjugate has one of the following structures (IX)

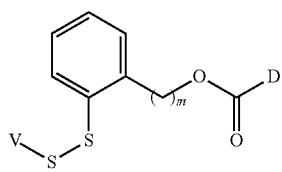

(IX)

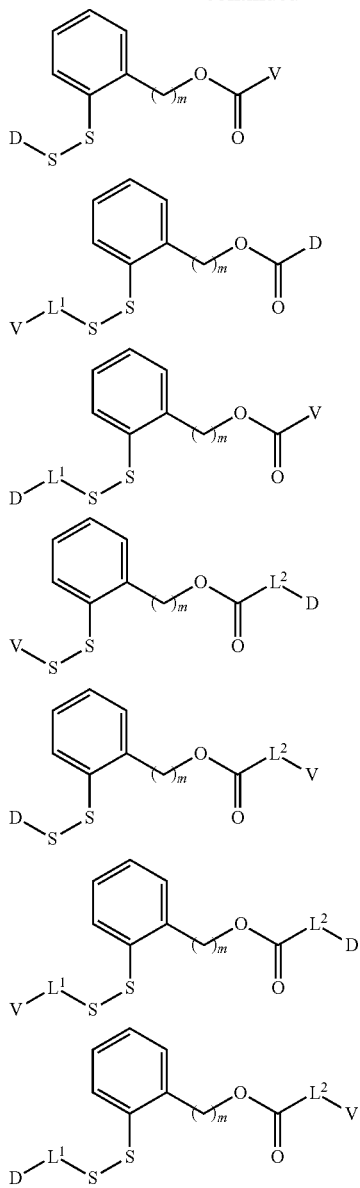

wherein m is an integer from 1 to about 4; $X^1$ and $X^2$ are each independently selected leaving groups; and $L^1$ and $L^2$ are each independently selected bivalent linkers.

In another embodiment, the conjugate has one of the following structures (X)

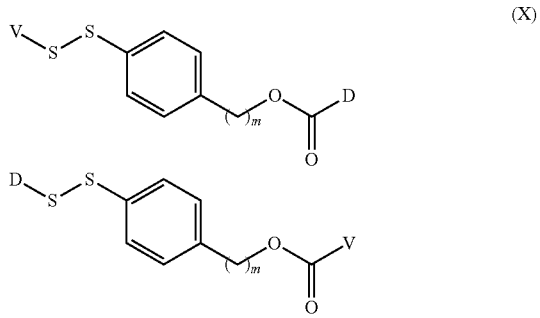

(X)

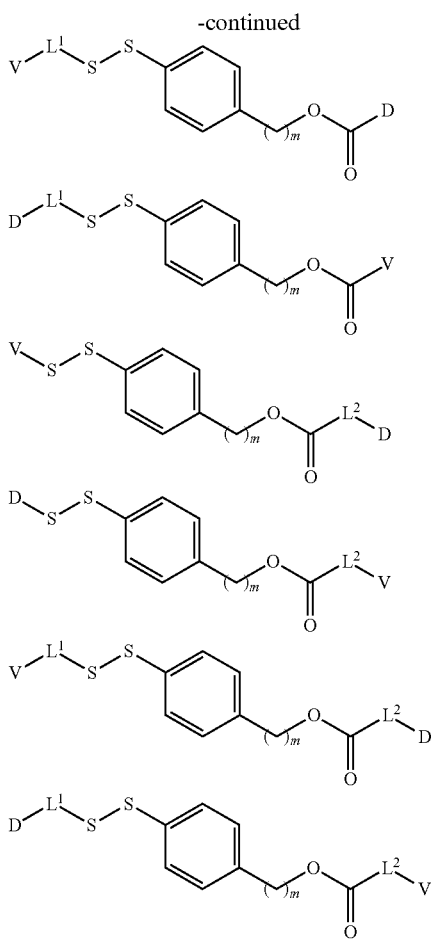

wherein m is an integer from 1 to about 4; $X^1$ and $X^2$ are each independently selected leaving groups; and $L^1$ and $L^2$ are each independently selected bivalent linkers.

DETAILED DESCRIPTION

Figure 1A:
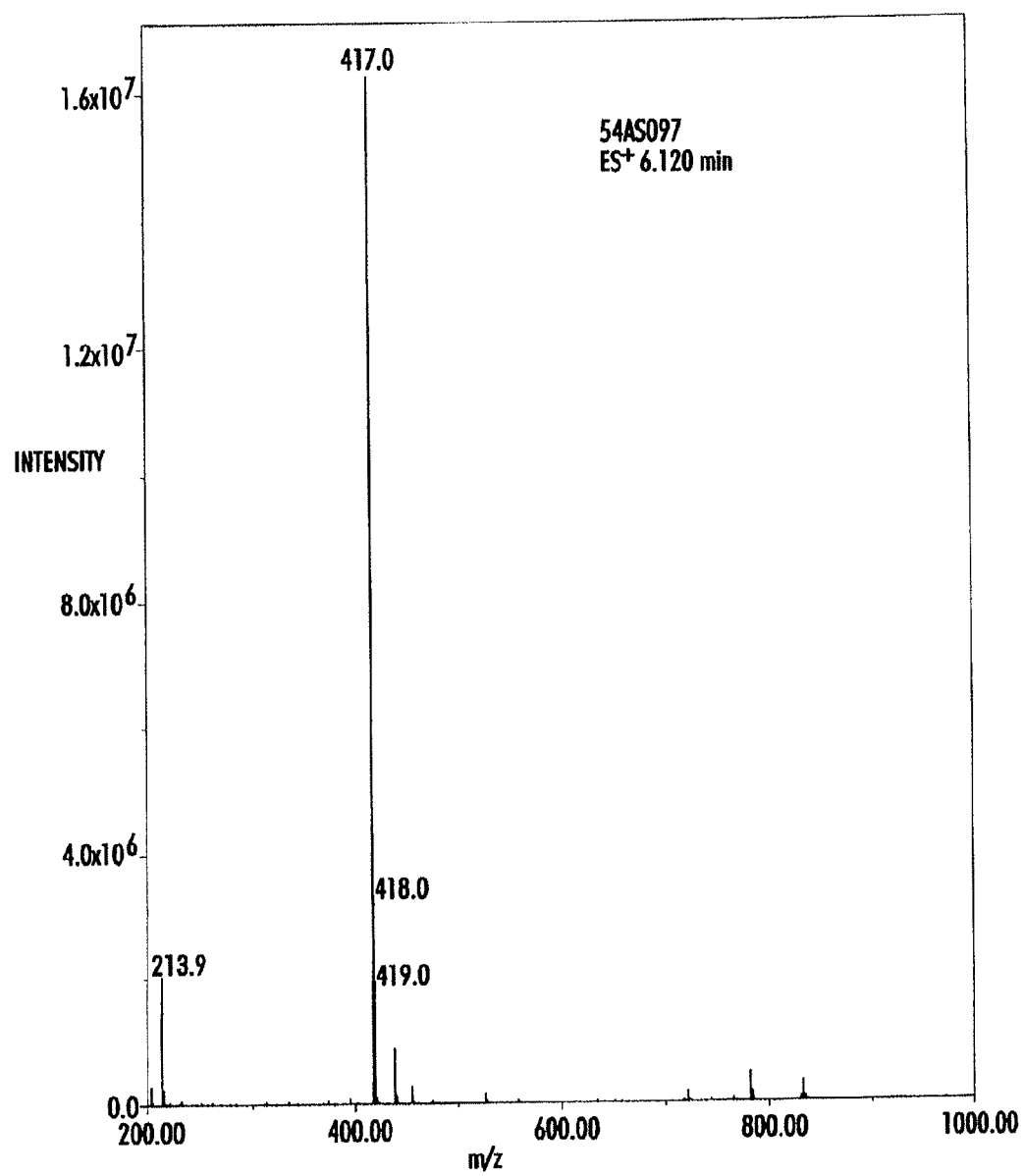
FIG. 1a shows the mass spectrum of Example 1, compound 5.
Figure 1B:
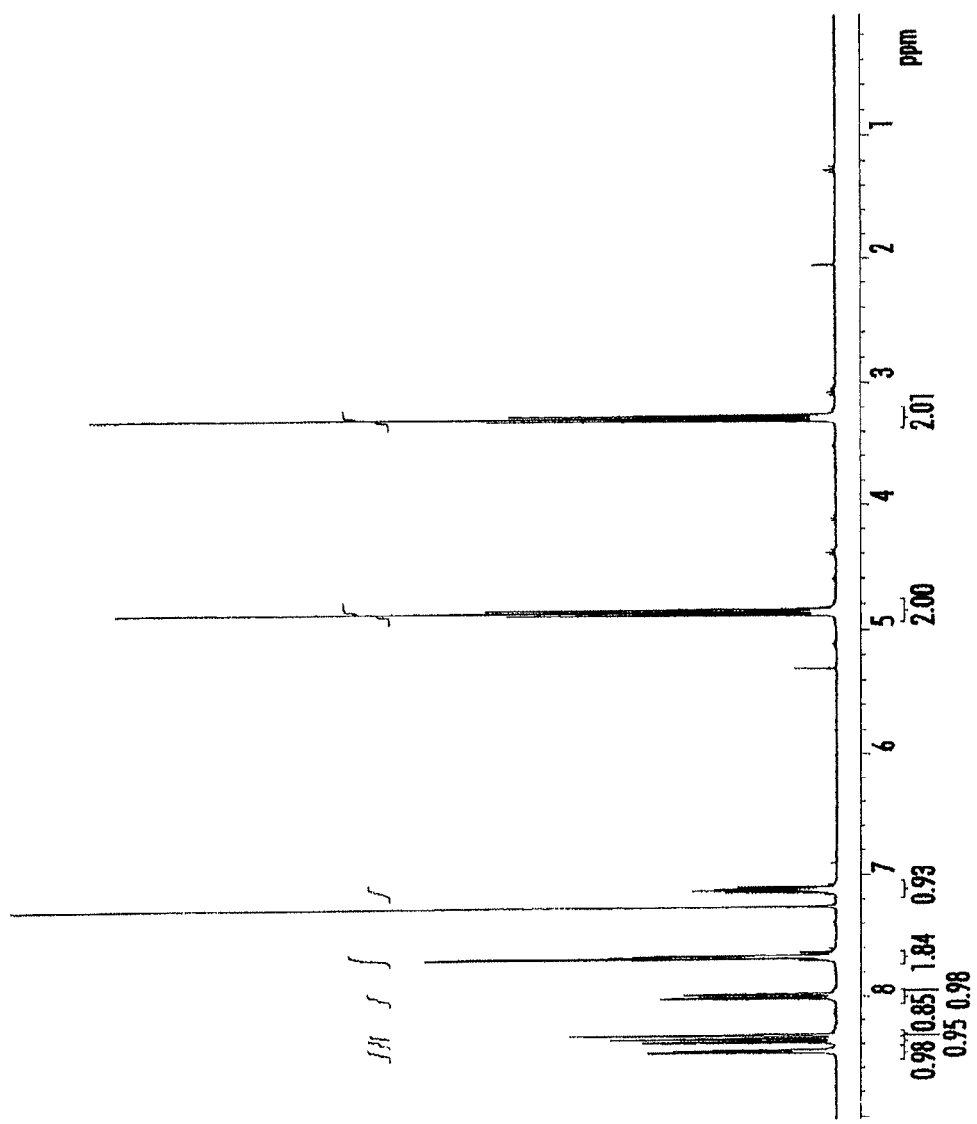
FIG. 1b shows the $^1$H NMR spectrum of Example 1, compound 5.
Figure 2:
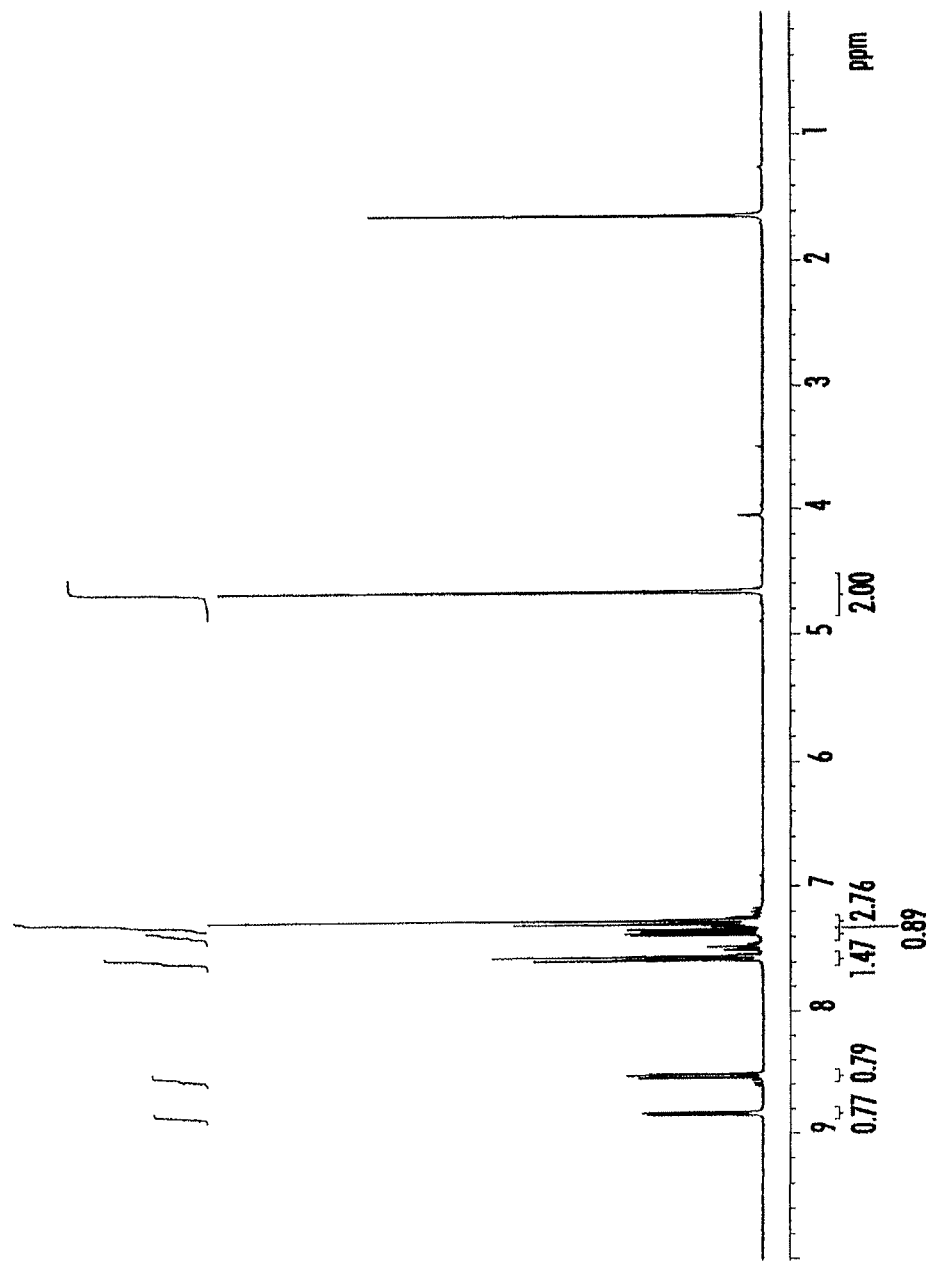
FIG. 2 shows the $^1$H NMR spectrum of Example 3, compound 10.
Figure 3:
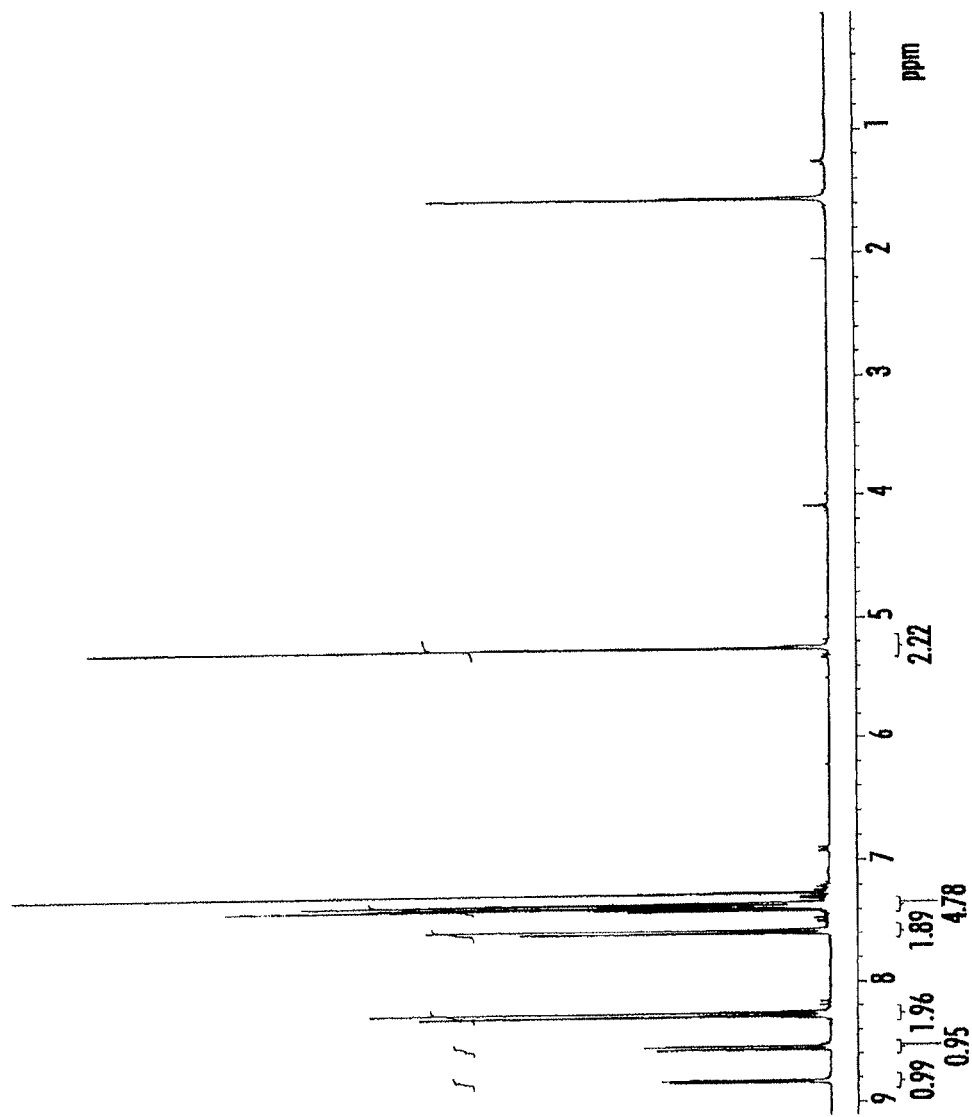
FIG. 3 shows the $^1$H NMR spectrum of Example 4, compound 12.

Bivalent linkers for use in conjugates or for use in preparing conjugates are described herein. The bivalent linkers may be used to prepare drug conjugates, imaging agent conjugates, and/or diagnostic agent conjugates. Drug conjugates include targeting agent conjugates, such as the vitamin receptor-binding drug conjugates as described in U.S. Patent Application Publication No. US-2005-0002942-A1, and other drug conjugates described in U.S. Patent Application Publications Nos. US-2001-0031252-A1 and US-2003-0086900-A1. Imaging agent conjugates and diagnostic agent conjugates include those described in U.S. Patent Application Publication No. US-2004-0033195-A1 and International Patent Application Publication No. WO 03/097647. The disclosures of each of the foregoing patent application publications are incorporated herein by reference.

It is appreciated that conjugates of analogs and derivatives of drugs, conjugates of analogs and derivatives of vitamins, conjugates of analogs and derivatives of imaging agents, and conjugates of analogs and derivatives of diagnostic agents may be prepared using the bivalent linkers described herein. Further, unless otherwise indicated, the term drug should be understood to include analogs and derivatives thereof, the term vitamin should be understood to include analogs and derivatives thereof, the term imaging agent should be understood to include analogs and derivatives thereof, and the term diagnostic agent should be understood to include analogs and derivatives thereof.

The bivalent linkers described herein may be used as spacers to alter the overall distance from the drug, vitamin, imaging agent, or diagnostic agent and the moiety to which it is conjugated. Further, the bivalent linkers described herein may be used to alter the physicochemical properties, solubility properties, and other properties of the drug, vitamin, imaging agent, or diagnostic agent conjugates in which they are included.

Illustratively, the bivalent linkers described herein may by included in linkers used to prepare vitamin receptor-binding drug conjugates, vitamin receptor-binding imaging agent conjugates, and vitamin receptor-binding diagnostic agent conjugates of the formulae (I)

V-L-D

V-L-IA

V-L-DA  (I)

where V is a vitamin receptor-binding moiety, including analogs or derivatives thereof, L is a linker, D is a drug, including analogs or derivatives thereof, IA is an imaging agent, including analogs or derivatives thereof, and DA is a diagnostic agent, including analogs or derivatives thereof. Linker (L) can comprise multiple bivalent linkers, including the bivalent linkers described herein.

In one embodiment, the bivalent linkers described herein are compounds of formulae (II)

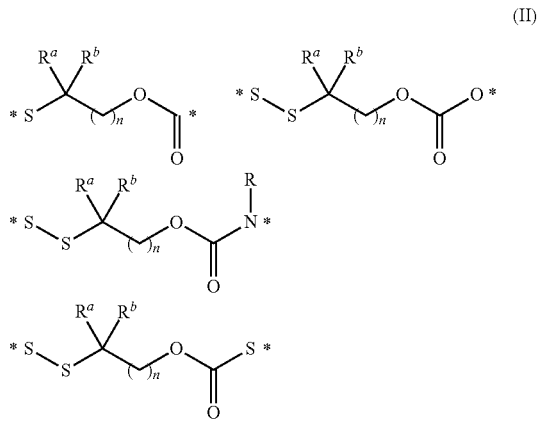

(II)

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the bivalent linkers described herein include compounds of formulae (III)

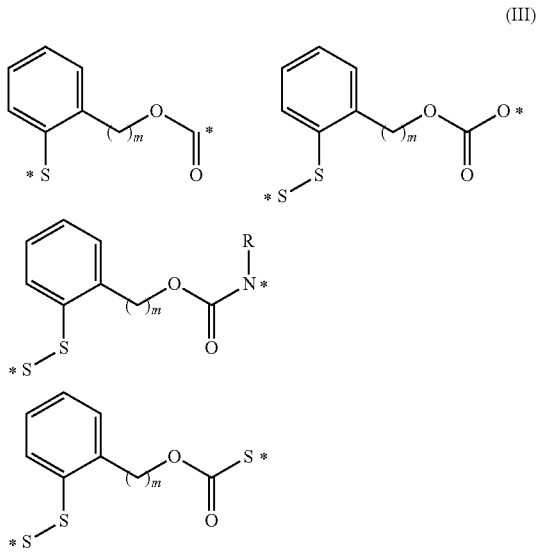

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the bivalent linkers described herein include compounds of formulae (IV)

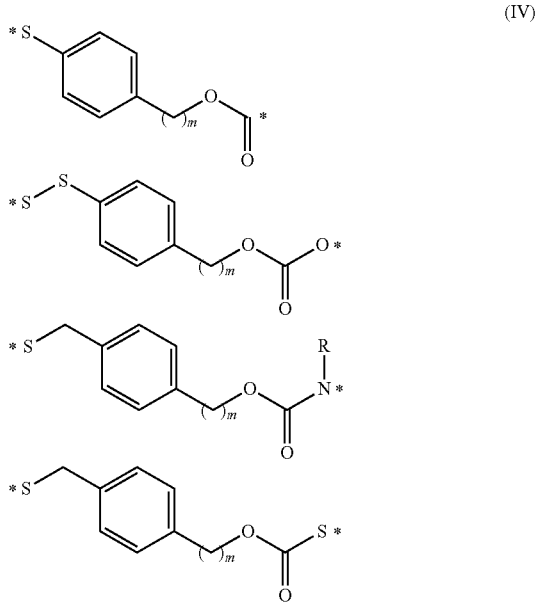

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the bivalent linkers described herein include compounds of formulae (V), (VI), and (VII)

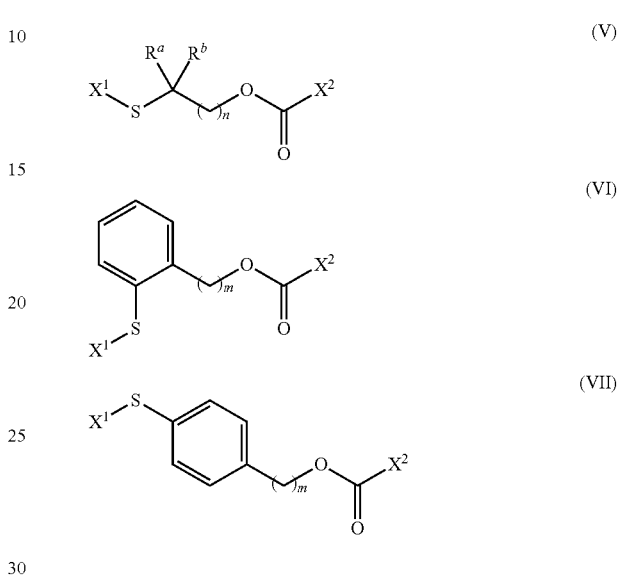

wherein n and m are each independently selected integers from 1 to about 4; $R^a$ and $R^b$ are each independently selected from the group consisting of hydrogen and alkyl, including lower alkyl such as $C_1$-$C_4$ alkyl that are optionally branched; or W and $R^a$ and $R^b$ are taken together with the attached carbon atom to form a carbocyclic ring; and $X^1$ and $X^2$ are each independently selected leaving groups that may be nucleophilically displaced by a drug, vitamin, imaging agent, diagnostic agent, another bivalent linker, or another part of the conjugate.

Illustratively, vitamin-drug conjugates that may be formed from the bivalent linkers described herein include compounds of formulae (VIII)

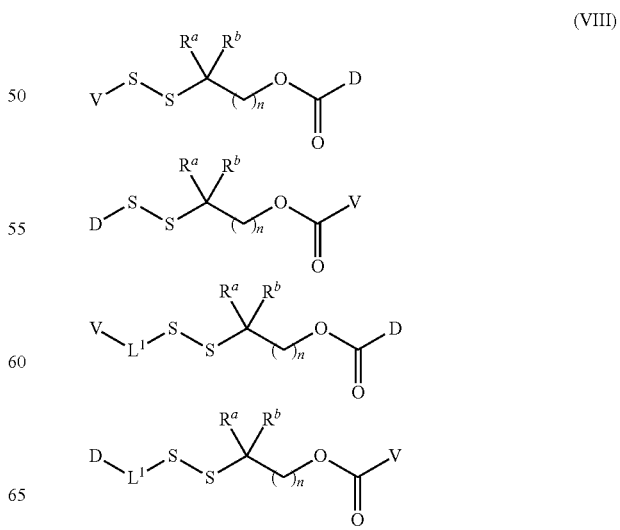

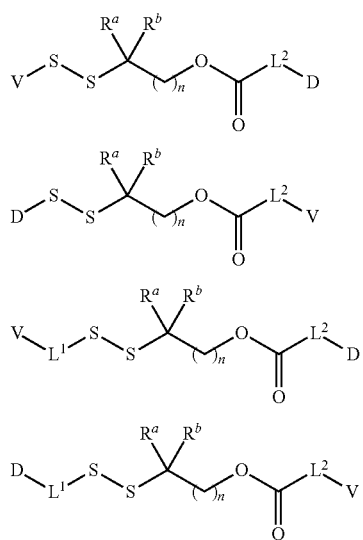

where V, D, and n are as described herein; n is an integer from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; and $L^1$ and $L^2$ are each independently selected bivalent linkers used to prepare the conjugates. Similarly, it is understood that the vitamin-imaging agent and vitamin-diagnostic agent conjugates corresponding to the formulae (VIII) may also be formed from the bivalent linkers described herein.

Illustratively, vitamin-drug conjugates that may be formed from the bivalent linkers described herein include compounds of formulae (IX)

(IX)

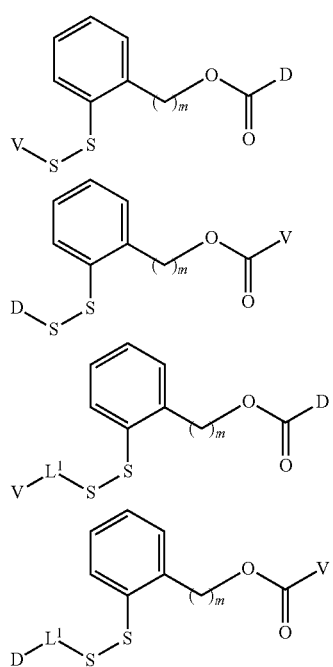

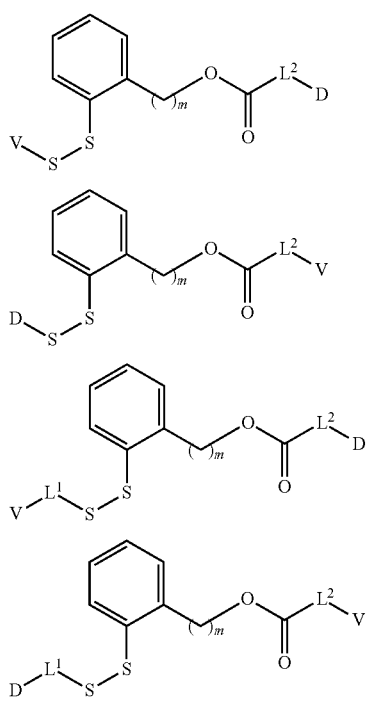

where V, D, and n are as described herein; m is an integer from 1 to about 4; and $L^1$ and $L^2$ are each independently selected bivalent linkers used to complete the conjugates. Similarly, it is understood that the vitamin-imaging agent and vitamin-diagnostic agent conjugates corresponding to the formulae (IX) may also be formed from the bivalent linkers described herein.

Illustratively, vitamin-drug conjugates that may be formed from the bivalent linkers described herein include compounds of formulae (X)

(X)

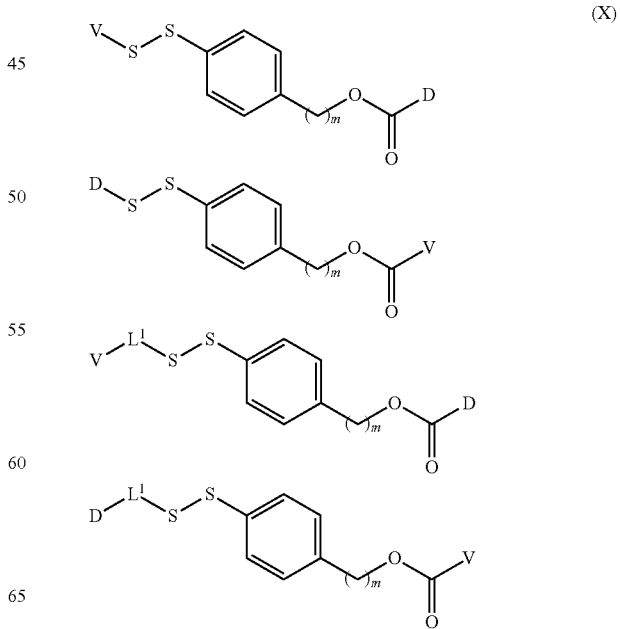

-continued

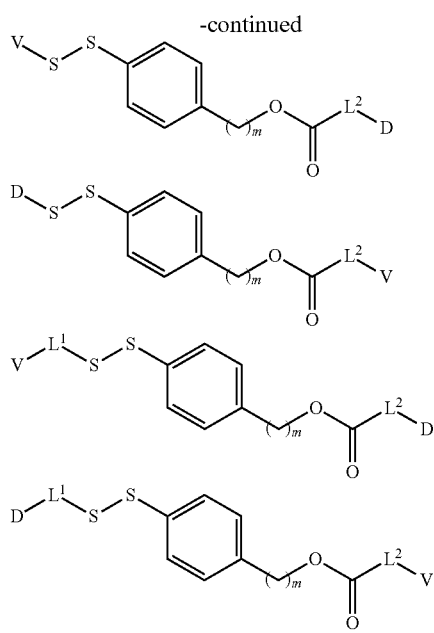

where V, D, and n are as described herein; m is an integer from 1 to about 4; and $L^1$ and $L^2$ are each independently selected bivalent linkers used to complete the conjugates. Similarly, it is understood that the vitamin-imaging agent and vitamin-diagnostic agent conjugates corresponding to the formulae (X) may also be formed from the bivalent linkers described herein.

It is to be further understood that when any of V, $L^2$, and/or D is connected to the carbonyl group of the bivalent linkers described herein, such as the bivalent linkers of formulae (VIII), (IX), and/or (X), the connection is made through a heteroatom, such as an oxygen, sulfur, optionally substituted nitrogen, and the like.

In another illustrative embodiment, intermediates useful for preparing drug, vitamin, imaging agent, or diagnostic agent conjugates are described herein. Such intermediates may be subsequently linked to other components to form vitamin, imaging agent, or diagnostic agent conjugates. Intermediates described herein include compounds of formulae XI

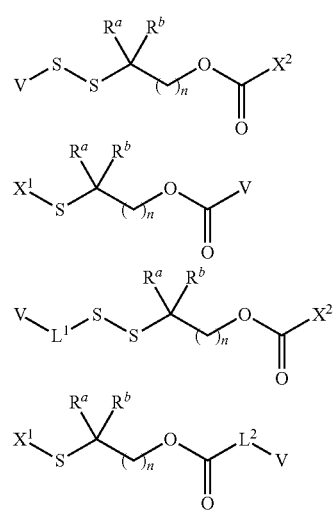

(XI)

-continued

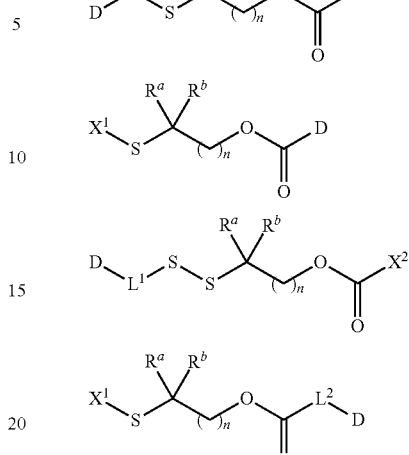

where V, D, $L^1$, $L^2$, $X^1$, and $X^2$ are as described herein; and n is an integer from 1 to about 4. Similarly, it is understood that the vitamin-imaging agent and vitamin-diagnostic agent conjugates corresponding to the formulae (XI) may also be formed from the bivalent linkers described herein.

Illustratively, vitamin-drug conjugates that may be formed from the bivalent linkers described herein include compounds of formulae (XII)

(XII)

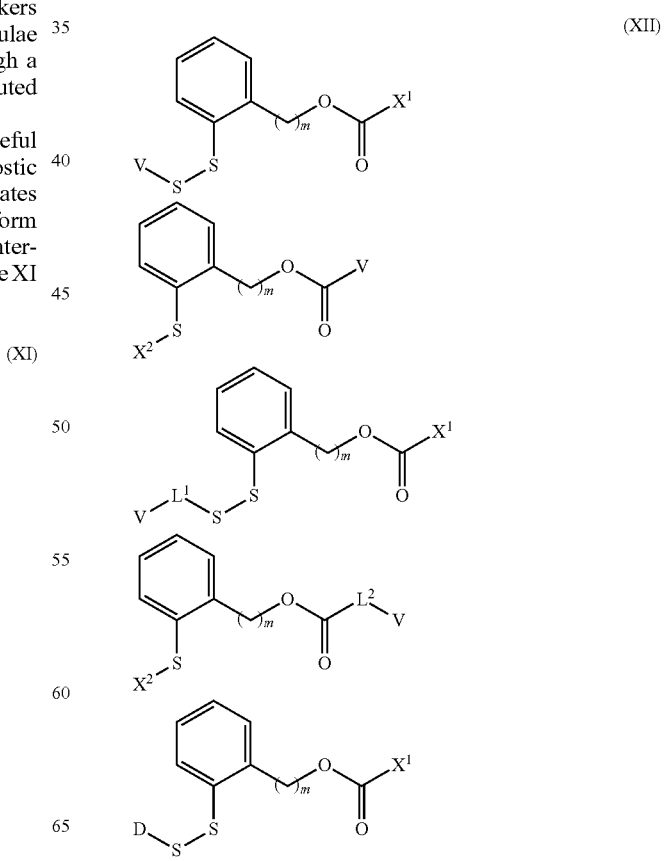

-continued

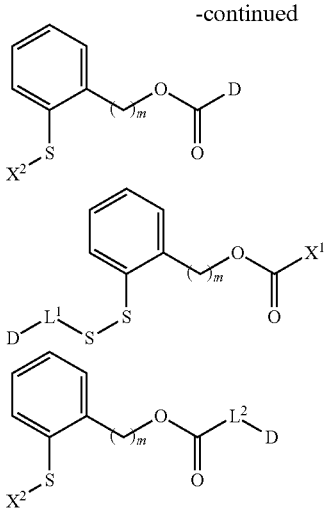

where V, D, $L^1$, $L^2$, $X^1$, and $X^2$ are as described herein; and m is an integer from 1 to about 4. Similarly, it is understood that the vitamin-imaging agent and vitamin-diagnostic agent conjugates corresponding to the formulae (XII) may also be formed from the bivalent linkers described herein.

Illustratively, vitamin-drug conjugates that may be formed from the bivalent linkers described herein include compounds of formulae (XIII)

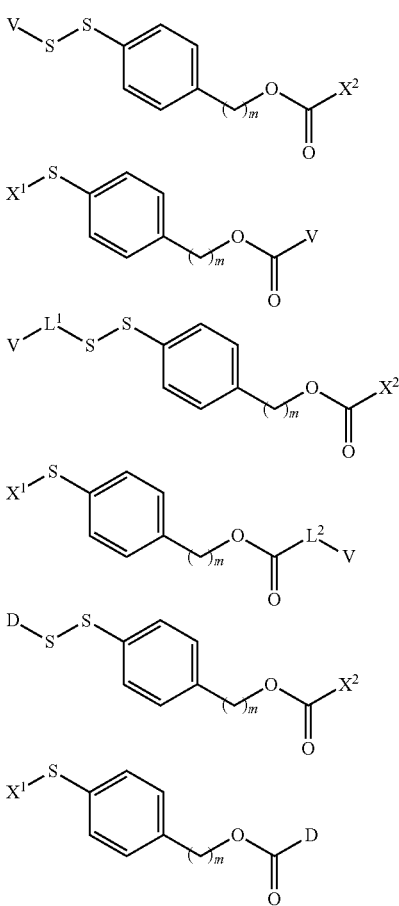

(XIII)

-continued

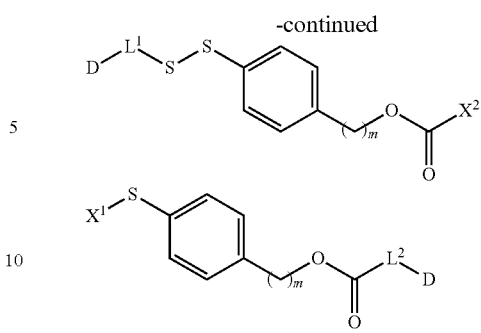

where V, D, $L^1$, $L^2$, $X^1$, and $X^2$ are as described herein; and m is an integer from 1 to about 4. Similarly, it is understood that the vitamin-imaging agent and vitamin-diagnostic agent conjugates corresponding to the formulae (XIII) may also be formed from the bivalent linkers described herein.

It is further understood that when any of V, $L^2$, and/or D is connected to the carbonyl group of the bivalent linkers described herein, such as the bivalent linkers of formulae (XI), (XII), and (XIII), the connection is made through a heteroatom, such as an oxygen, sulfur, optionally substituted nitrogen, and the like.

In one illustrative embodiment, the leaving group $X^1$ is an arylthio group. In one aspect, the arylthio group is an heteroarylthio group and includes, but is not limited to, optionally substituted 2-pyridinylthio, optionally substituted 4-pyridinylthio, and the like. In another illustrative aspect, the substitutions include electron withdrawing substituents, such as cyano, nitro, alkylsulfonyl, arylsulfonyl, halo, haloalkyl, acyl and derivatives thereof, carboxyl and derivatives thereof, and the like, and combinations thereof.

In another illustrative embodiment, the leaving group $X^2$ is an aryloxy group. In one aspect, the aryloxy group is an optionally substituted phenyl group. In another illustrative aspect, the aryloxy group is an optionally substituted heteroaryloxy group and includes, but is not limited to, optionally substituted benzotriazoles, and the like. In another illustrative aspect, the substitutions include electron withdrawing substituents, such as cyano, nitro, alkylsulfonyl, arylsulfonyl, halo, haloalkyl, acyl and derivatives thereof, carboxyl and derivatives thereof, and the like, and combinations thereof.

Illustrative leaving groups $X^1$ include compounds of formulae (XIV)

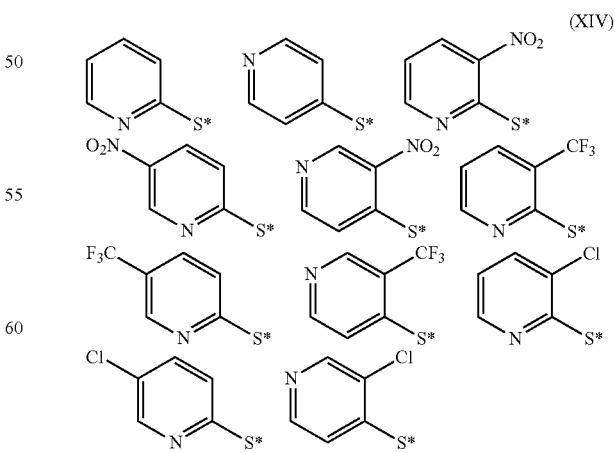

(XIV)

where (*) indicates the point of attachment to the sulfur of the bivalent linkers described herein. In one aspect, each of the leaving groups $X^1$ having the formulae (XIV) may be optionally substituted with one or more substituents, or additional substituents, selected from halo, alkyl, haloalkyl, alkoxy, haloalkoxy, cyano, nitro, and the like. Further illustrative leaving groups include alkyl and arylsulfonyl leaving groups, such as but not limited to

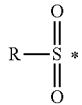

where R is alkyl or aryl, each of which may be optionally substituted, such as with halo, alkyl, haloalkyl, alkoxy, haloalkoxy, cyano, nitro, and the like; and where (*) indicates the point of attachment to the sulfur of the bivalent linkers described herein.

Illustrative leaving groups $X^2$ include compounds of formulae (XV)

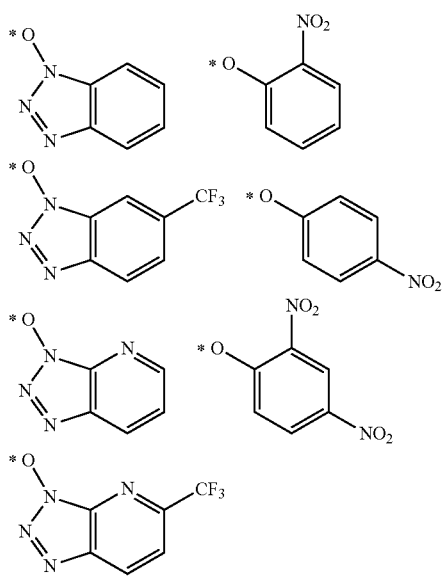

(XV)

where (*) indicates the point of attachment to the carbonyl of the bivalent linkers described herein. In one aspect, each of the leaving groups $X^2$ having the formulae (XV) may be optionally substituted with one or more substituents, or additional substituents, selected from halo, alkyl, haloalkyl, alkoxy, haloalkoxy, cyano, nitro, and the like.

Bivalent linkers that include leaving groups such as those shown in formulae XIII, XIV, and XV may be prepared following the corresponding synthetic procedures described in the Examples described herein.

In another illustrative aspect, the vitamin receptor binding drug delivery conjugate intermediate described herein includes a compound having the formulae:

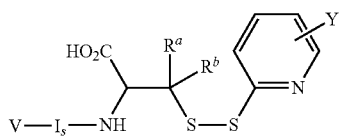

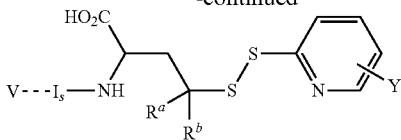

or a protected derivative thereof, where $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; Y is hydrogen or a substituent, illustratively an electron withdrawing substituent, including but not limited to nitro, cyano, halo, alkylsulfonyl, a carboxylic acid derivative, and the like; $I_s$ is either a bond or another bivalent linker; and where V is as defined herein. It is appreciated that other substituents may be optionally present on the cysteine or homocysteine portion of these drug delivery conjugates, such as longer and/or branched alkyl groups, alkoxy groups, alkoxyalkyl groups, and the like. It is to be understood that cyclic variants of the cysteine portion of these drug delivery conjugates are contemplated. In one aspect, $R^a$ is hydrogen, and $R^b$ is alkyl, such as methyl. In another aspect, both le and $R^b$ are alkyl, either the same or different, such as both being methyl. In another aspect, $R^a$ and $R^b$ are taken together with attached carbon to form a spiro cyclopropyl.

In another illustrative aspect of the vitamin receptor binding drug delivery conjugate intermediate described herein, the intermediate includes compounds having the formulae:

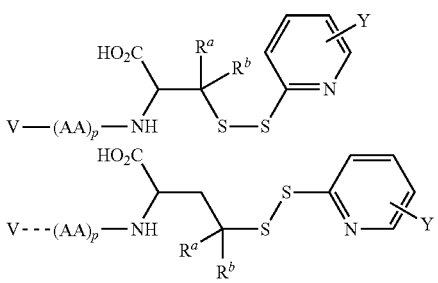

or protected derivatives thereof, where V is the vitamin, or an analog or a derivative thereof, AA is an amino acid, illustratively selected from the naturally occurring amino acids, or stereoisomers thereof, $R^a$ and $R^b$ are each independently selected from the group consisting of hydrogen and alkyl, including lower alkyl such as $C_1$-$C_4$ alkyl that are optionally branched, or $R^a$ and $R^b$ are taken together with the attached carbon atom to form a carbocyclic ring, Y is hydrogen or a substituent, illustratively an electron withdrawing substituent, including but not limited to nitro, cyano, halo, alkylsulfonyl, a carboxylic acid derivative, and the like, n and m are independently selected integers, such as 1, 2, or 3, and p is an integer such as 1, 2, 3, 4, or 5. It is appreciated that other substituents may be optionally present on the cysteine or homocysteine portion of these drug delivery conjugates, such as longer and/or branched alkyl groups, alkoxy groups, alkoxyalkyl groups, and the like. It is to be understood that cyclic variants of the cysteine portion of these drug delivery conjugates are contemplated. AA can also be any other amino acid, such as any amino acid having the general formula:

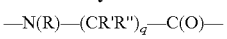

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In another illustrative aspect of the vitamin receptor binding drug delivery conjugate intermediate described herein, the drug, or an analog or a derivative thereof, includes an alkylthiol nucleophile.

It is appreciated that the bivalent linkers described herein may undergo cleavage under certain chemical, environmental, or physiological conditions. In particular, the bivalent linkers described herein may undergo cleavage under physiological conditions, such as by the action of a glutathione mediated mechanism. In such embodiments, those linkers may be alternatively referred to as releasable linkers.

Illustrative mechanisms for cleavage of the bivalant linkers described herein include the following 1,4 and 1,6 fragmentation mechanisms

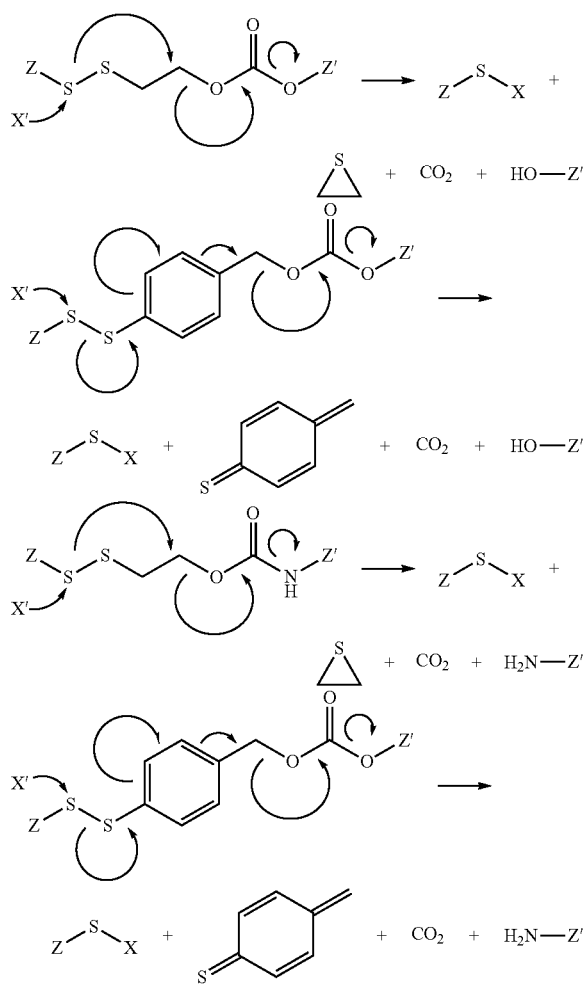

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the bivalent linker. It is to be understood that although the above fragmentation mechanisms are depicted as concerted mechanisms, any number of discrete steps may take place to effect the ultimate fragmentation of the bivalent linker to the final products shown. For example, it is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing bivalent linkers, following an illustrative breaking of the disulfide bond, the resulting phenyl thiolate may further fragment to release a carbonic acid or carbamic acid moiety by forming a resonance stabilized intermediate. In any of these cases, the releaseable nature of the illustrative bivalent linkers described herein may be realized by whatever mechanism may be relevant to the chemical, metabolic, physiological, or biological conditions present.

General Disulfide Formation

Disulfide groups can be generally formed by reacting an alkyl or aryl sulfonylthioalkyl derivative, or the corresponding heteroaryldithioalkyl derivative such as a pyridin-2-yldithioalkyl derivative, and the like, with an alkylenethiol derivative, as illustrated in Scheme 1.

Scheme 1

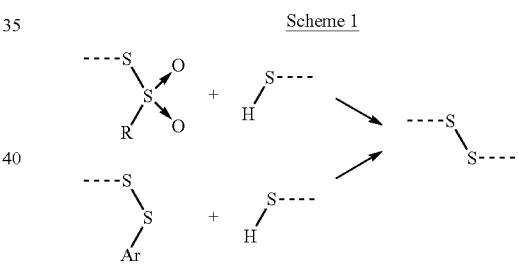

Solvents that can be used for this reaction include THF, EtOAc, $CH_2Cl_2$, $CHCl_3$, $CCl_4$, DMF, DMSO, and the like. The temperature range employed in this transformation may vary between 0° C. and 80° C. The required alkyl or aryl sulfonylthioalkyl derivative may be prepared using art-recognized protocols, and also according to the method of Ranasinghe and Fuchs, Synth. Commun. 18(3), 227-32 (1988), the disclosure of which is incorporated herein by reference. Other methods of preparing unsymmetrical dialkyl disulfides are based on a transthiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference.

General Carbonate Thiocarbonate and Carbamate Formation

Carbonates, thiocarbonates, and carbamates can generally be formed by reacting an hydroxy-substituted compound, a thio-substituted compound, or an amine-substituted compound, respectively, with an activated alkoxycarbonyl derivative where X is a suitable leaving group, as illustrated in Scheme 2.

Scheme 2

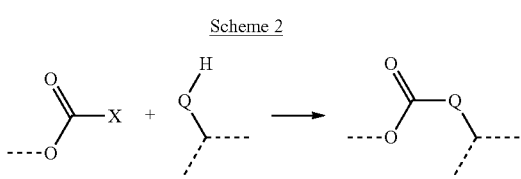

where Q is oxygen, sulfur, optionally substituted nitrogen, optionally protected nitrogen, and the like. Solvents that can be used for this reaction include THF, EtOAc, $CH_2Cl_2$, $CHCl_3$, $CCl_4$, DMF, DMSO, and the like. The temperature range employed in this transformation may vary between 0° C. and 80° C. Any basic catalyst such as an inorganic base, an amine base, a polymer bound base, and the like can be used to facilitate the reaction.

EXAMPLES

Example 1

6-Trifluoromethyl-1-[2-(2-pyridinyldithio)ethoxycarbonyloxy]benzotriazole

Example 1 was prepared according to Scheme 3.

Scheme 3

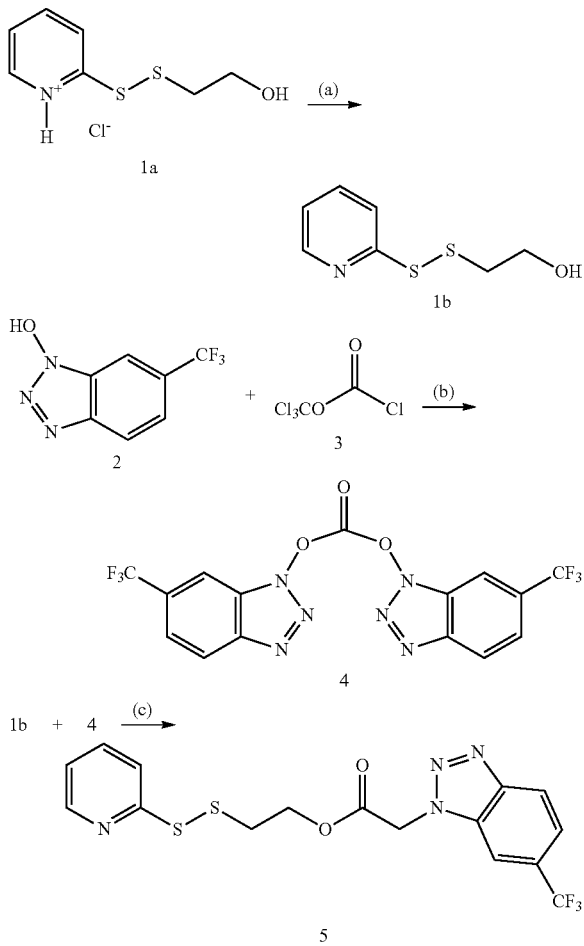

(a) 4-dimethylaminopyridine (DMAP), $CH_2Cl_2$; (b) $Et_2O$; (c) $CH_3CH$.

Step (a). A solution of 4-(dimethylamine)pyridine (3.0 g; 24.68 mmol; 1.03 eqs.) in 10 mL anhydrous methanol was added to a suspension of 2-(2-pyridyldithio)ethanol hydrochloride (compound (1a); $C_7H_9NS_2O.HCl$; 5.4 g; 24 mmol) in 10 ml of anhydrous methanol, and the mixture was stirred to form a clear solution. Within a few minutes, the solution turned turbid with the formation of a fine suspension, and this suspension was purified by flash chromatography (FC). FC was performed by using 140 g silica gel 60 with 5% methanol in $CH_2Cl_2$ to form a 24 cm×4.3 cm silica gel bed with 500 ml solvent reservoir. The said suspension in 20 mL $CH_2Cl_2$ was loaded and the column was eluted with 5% methanol in $CH_2Cl_2$ with standard collection of 30 mL fractions coupled with UV-detection. The product compound (1b) can be detected from fraction 2 to 9 by TLC (1:1 Hexane: EtOAc).

Step (b). 1-Hydroxy-6-(trifluoromethyl)benzotriazole (compound (2); $C_7H_4F_3N_3O$; 2.3 g; 0.11 mol; Aldrich) was dissolved in 770 mL ether and the supernatant was decanted into a 2L RB flask Trichloromethyl chloroformate (compound (3); $C_2Cl_4O_2$; 107 g; 0.053 mol; 6.0 mL) was added into this clean colorless solution at room temperature over a 15 minutes period. The mixture was gently heated to temperature between 40-50° C. for 1 hour, and cooled to room temperature. The solution was filtered, and the precipitate was washed with ether (10×30 mL). The precipitate was a white powder and was dried with vacuum and gave 16.95 g (74% yield). Additional synthetic details are described by Ogura et al, in *Synthesis,* 1987, 557-560, the disclosure of which is incorporated herein by reference.

Step (c). A solution of compound (1b) (ca. 7.5 mmol) in 10 mL acetonitrile was added over a 2 minutes period to a stirred clean solution of compound 4 (3.46 g; 8 mmol) in 300 ml acetonitrile at room temperature. The mixture was then stirred at room temperature for 24 hours. TLC analysis of the mixture was performed after 24 hours. The mixture was allowed to be stirred for additional 14 hours to a total of 38 hours. The mixture was concentrated and washed with 50 mL of IN $NaHCO_3$ eq. and 100 mL of ethyl acetate. The organic layer was separated, washed further with 1 N $NaHCO_3$ eq. (1×10 mL), dried ($Na_2SO_4$), and filtered, to give a white solid powder, which was dried on vacuum for 5 hours and gave 2.54 g.

Example 2

Example 2 was prepared according to Scheme 4.

Scheme 4

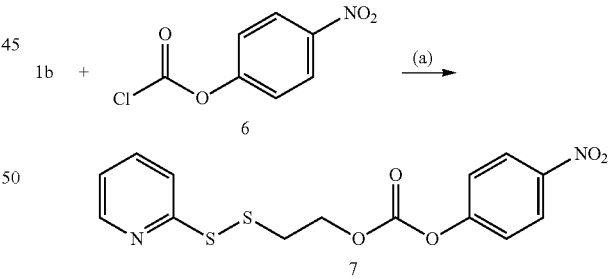

(a) pyridine, $CH_2Cl_2$.

2-(2-pyridyldithio)ethanol hydrochloride (compound (1b); 8.8 g; 39.33 mL) was dissolved in 78 mL $CH_2Cl_2$, and 2 eqs. of pyridine ($C_5H_5N$; $1_5N$; 80.88 mL) was added. para-Nitrophenyl chloroformate (compound (6); 8.08 g; 40 mmol) was dissolved in 80 mL $CH_2Cl_2$, and the solution was added to mixture of 2-(2-pyridyldithio)ethanol hydrochloride and pyridine over a 15 minutes period. The resultant clear solution was stirred at room temperature for 15 hours. TLC analysis for the above mixture after 15 hours stirring indicated completion of the reaction. The mixture was then filtered to remove precipitated pyridine hydrochloride. The light yellow clear filtrate was washed with deionized water (2×50 mL) to remove the dissolved pyridine hydrochloride, dried (Na$_2$SO$_4$), filtered, and concentrated with vacuum (13.8 g). Silica gel 60 (250 g) in CH$_2$Cl$_2$ was used to from a 50 cm×4.2 cm of silica gel bed with 250 mL solvent reservoir. The product compound (7), ca. 13.8 g, was dissolved in 15 mL (10 mL +5 mL) of CH$_2$Cl$_2$ and the solution was loaded with an elution ratio of 30 mL/min with standard collection of 30 mL fractions coupled with UV-detection and gave 13.3 g (96% yield).

Example 3

Example 3 was prepared according to Scheme 5.

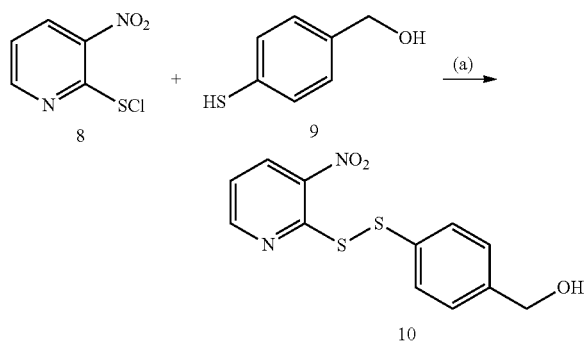

(a) anhydrous CH$_2$Cl$_2$.

3-Nitro-2-pyridinesulfenyl chloride (compound (8)) was dissolved in 15 mL anhydrous CH$_2$Cl$_2$. The solution was cooled by an ice bath. 4-ethanoyl thiophenol (compound (9)) was dissolved in 10 mL CH$_2$Cl$_2$ and added to a dropping funnel affixed to the container containing 3-nitro-2-pyridine-sulfenyl chloride solution. The solution of 4-ethanoyl thiophenol was added over a 2 to 5 minute period. After the solution of 4-ethanoyl thiophenol was added, the mixture was allowed to warm to room temperature and then stirred for 2 hours. While addition of 4-ethanoyl thiophenol, a precipitate formed. After the 2 hours period of stirring at room temperature was completed, the mixture was sonicated for 5 minutes and the precipitate dissolved. TLC analysis showed a new spot formed in addition to 3-nitro-2-pyridinesulfenyl chloride and 4-ethanoyl thiophenol. The reaction mixture was washed with saturated NaHCO$_3$. The organic layer was supplemented with an addition 100 mL CH$_2$Cl$_2$. The product was dried for 3 hours under vacuum.

Example 4

Example 4 was prepared according to Scheme 6.

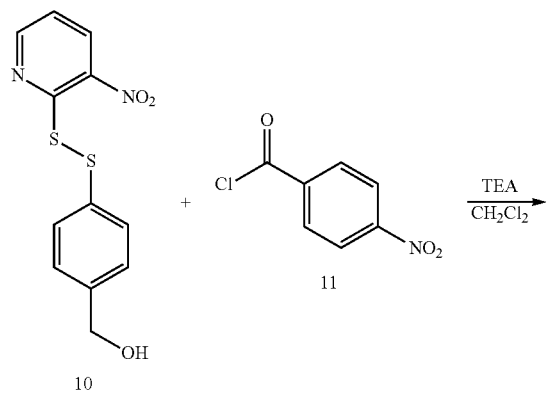

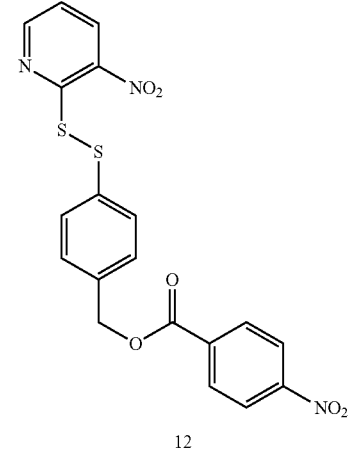

Compound (10) (0.025 g; 0.085 mmol) was dissolved in anhydrous CH$_2$Cl$_2$ under stirring. para-Nitrophenyl choloro-fornate (compound (11); 0.020 g; 1.2 eq.) was added along with 1 eq. of triethylamine (TEA) to the stirring solution. TLC analysis showed that compound (10) was consumed after 2 hours. The product compound (12) was isolated by column chromatography (7:3 Hexane: EtOAc).

Example 5

General preparation of compounds containing a cysteine disulfide bond

Any of thiosulfonates (13) (1 eq.), prepared according to the method of Ranasinghe and Fuchs, *Synth. Commun.* 18(3), 227-32 (1988), the disclosure of which is incorporated herein by reference, are reacted with drugs, drug analogs, or drug derivatives (14) (1 eq.) to prepare the drug thiosulfonates (15) as a solution in methanol, as shown in Scheme 7.

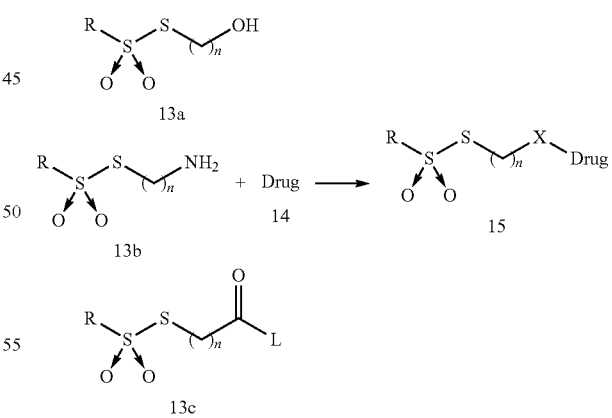

Referring to Scheme 7, R is alkyl or aryl, L is a suitable leaving group, such as halogen, pentafluorophenyl, and the like, n is an integer from 1 to about 4, and X is —O—, —NH—, —C(O)O—, or —C(O)NH—. Conversion is conveniently monitored by observing the disappearance of each starting material by TLC (silica gel; CHCl$_3$/MeOH=9/1). Final yield was 83% (mass of removed product was 32 mg from a total yield of 38.9 mg).

The folate-containing peptidyl fragment Pte-Glu-(AA)$_n$-Cys-OH (18) is prepared by a polymer-supported sequential approach using the Fmoc-strategy on an acid-sensitive Fmoc-Cys(Trt)-Wang resin (16), as shown in Scheme 8.

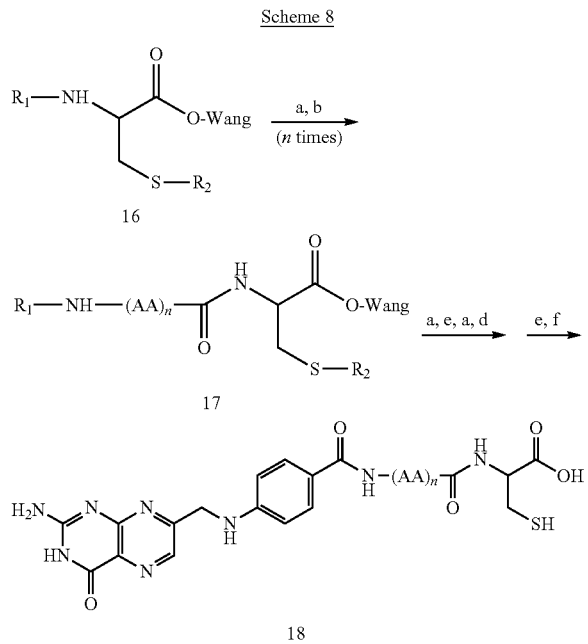

(a) 20% piperidine/DMF; (b) Fmoc—AA—OH, PyBop, DIPEA, DMF;
(c) Fmoc-Glu(O—t-Bu)—OH, PyBop, DIPEA, DMF; (d) 1. N$^{10}$(TFA)—Pte—OH; PyBop, DIPEA, DMSO; (e) TFAA, (CH$_2$SH)$_2$, i-Pr$_3$SiH;
(f) NH$_4$OH, pH 10.3.

Referring to Scheme 8, R$_1$ is Fmoc, R$_2$ is Trityl, and DIPEA is diisopropylethylamine. PyBop is applied as the activating reagent to ensure efficient coupling. Fmoc protecting groups are removed after each coupling step under standard conditions. Appropriately protected amino acid building blocks, such as Fmoc-Glu-OtBu, N$^{10}$-TFA-Pte-OH, and the like, are used, as described in Scheme 8, and represented by in step (b) by Fmoc-AA-OH. Thus, AA refers to any amino acid starting material, that is appropriatedly protected.

The coupling sequence (steps (a) & (b)) involving Fmoc-AA-OH is performed "n" times to prepare solid-supported peptide (17), where n is an integer and may equal 0 to about 100. Following the last coupling step, the remaining Fmoc group is removed, and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups. The TFA protecting group is removed upon treatment with base (step (f) to provide the folate-containing Cys-containing peptidyl fragment (18).

Drug conjugates are prepared by reacting folate derivative (18) (0.9-0.95 eq.) with drug thiosulfonate (15) in deionized water (0.04 M, pH adjusted to 7 with 0.1 N NaHCO$_3$) under argon for about 30 minutes, forming a disulfide bond. Upon evaporation of the methanol in vacua, the conjugate may be purified by preparative HPLC (Prep Novapak HR C18 19 X 300 mM column; mobile phase (A)-1.0 mM phosphate buffer, pH=6; organic phase (B)-acetonitrile; conditions-gradient from 99% A and 1% B to 50% A and 50% B in 30 minutes, flow rate=15 mL/minute).

Examples 6a-6f

Examples 6a-6f were prepared by the following general procedure. To a well stirred solution of the corresponding drug having an —OH group (1 eq. in dry CH$_2$Cl$_2$ or dry THF) was added under argon 6-(trifluoromethyl)benzotriazolyl 2-(2'-pyridyldithioethyl carbonate (1.3 eq.) and NN-dimethylaminopyridine (1.5 eq.). The reaction mixture was stirred for 3 h, and the pyridyldithio-derivatized drug was isolated by silica chromatography (>65% for each example). The corresponding peptidyl fragment (0.5 eq.), prepared according to the procedures described herein and alternatively by conventional procedures, such as those described in U.S. patent application No. US-2005-0002942-A1, was dissolved in DMSO. To the resulting clear yellow solution was added the pyridyl-dithio derivatized drug. After 30 min, the reaction was completed and the conjugate purified by HPLC. In the case of Example 6e, the peptidyl fragment Pte-Glu-Asp-Arg-Asp-Asp-Cys-OH was first dissolved in water, and the pH of the solution was adjusted to 2.5 with 0.1 N HCl, causing the peptidyl fragment to precipitate. The peptidyl fragment was collected by centrifugation, dried, and dissolved in DMSO for subsequent reaction with the pyridyldithio-derivatized drug.

Example 6a

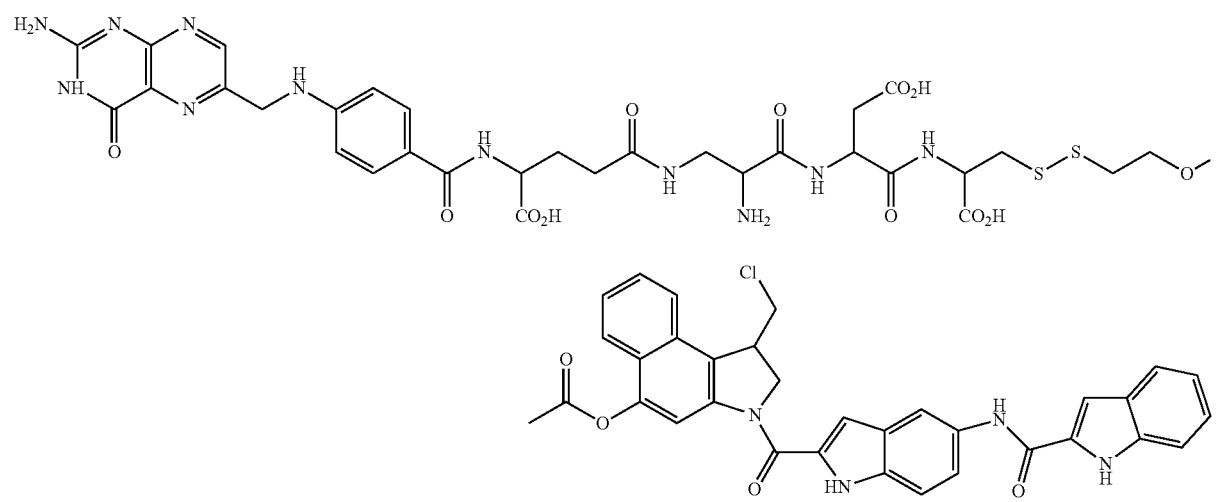

¹H NMR (DMSO-d₆) δ 4.7 (d, 1H), 4.95 (t, 1H), 6.7 (d, 4H), 6.9 (t, 1H), 7.95 (d, 2H), 8.1 (d, 2H), 8.2 (m, 1H), 8.3 (s, 1H), 8.4 (s, 1 H), 8.7 (s, 1H), 10.2 (s, 1H), 11.8 (d, 2H).
Example 6b
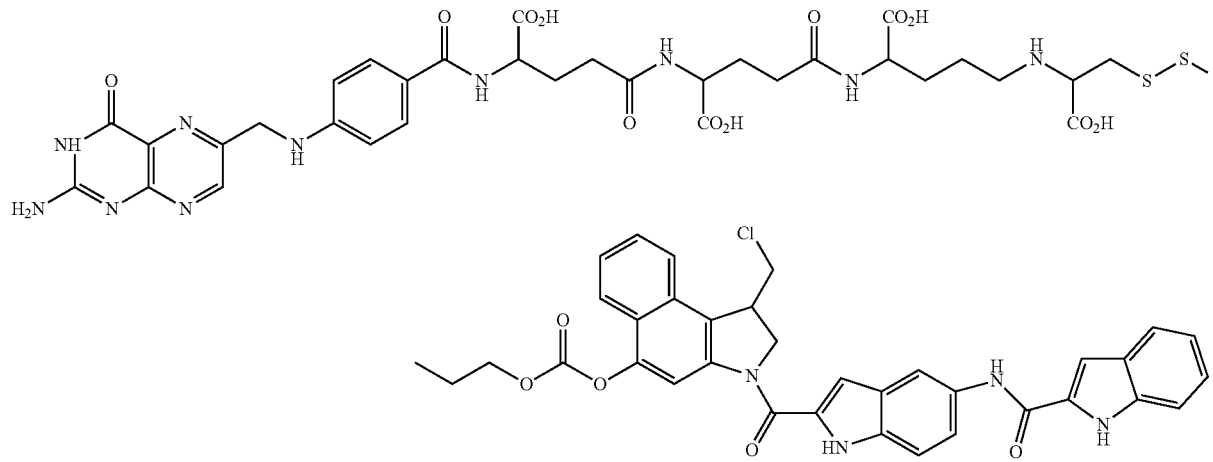
ES MS (m−H)⁻ 1436.4, (m+H)⁺ 1438.3.
Example 6c
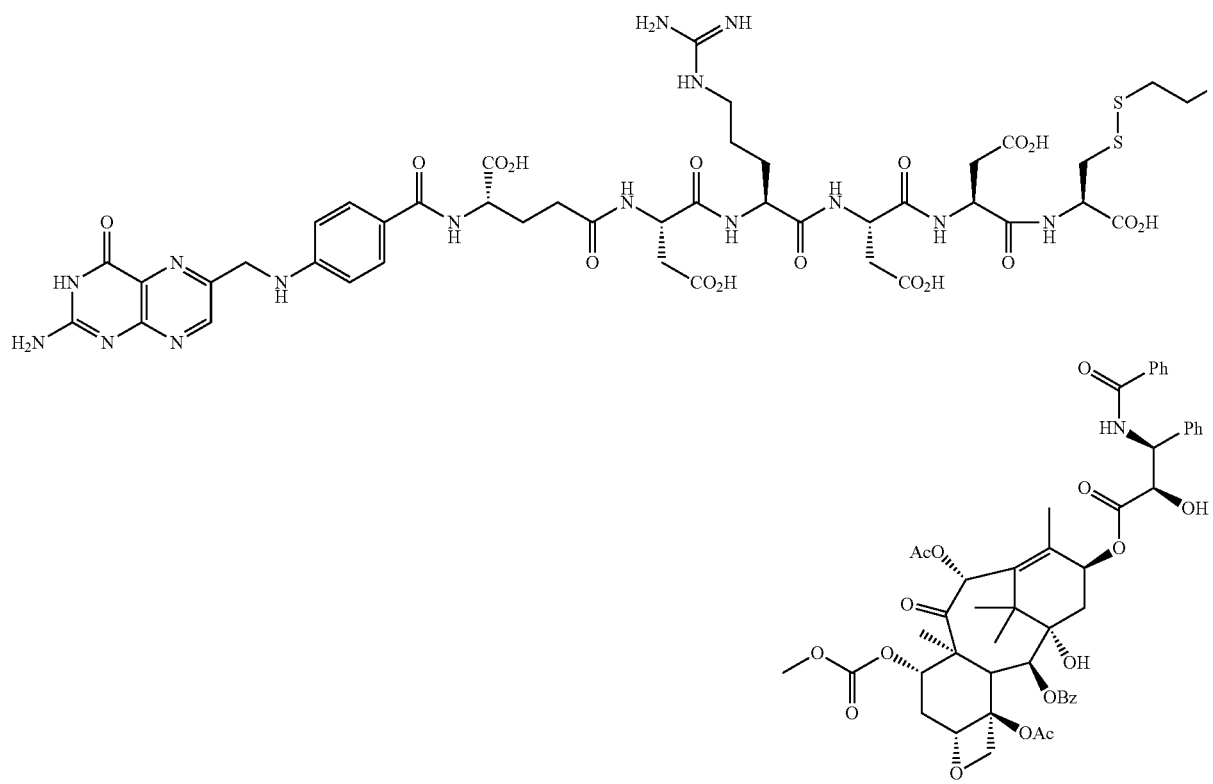
¹H NMR (DMSO-d₆/D₂O) δ 1.0 (s, 1H), 1.1 (s, 1H), 1.6 (s, 1H), 1.8 (s, 1H), 2.1 (s, 1H), 2.25 (s, 3H), 2.65 (dd, 2H), 3.7 (d, 1H), 4.4 (t, 1H), 4.55 (q, 2H), 4.6 (d, 2H), 4.95 (d, 1H), 5.9 (t, 1H), 6.15 (s, 1H), 6.6 (d, 2H), 7.85 (d, 2H), 7.95 (d, 2H), 8.6 (s, 1H), 8.95 (d, 1H).

Example 6d
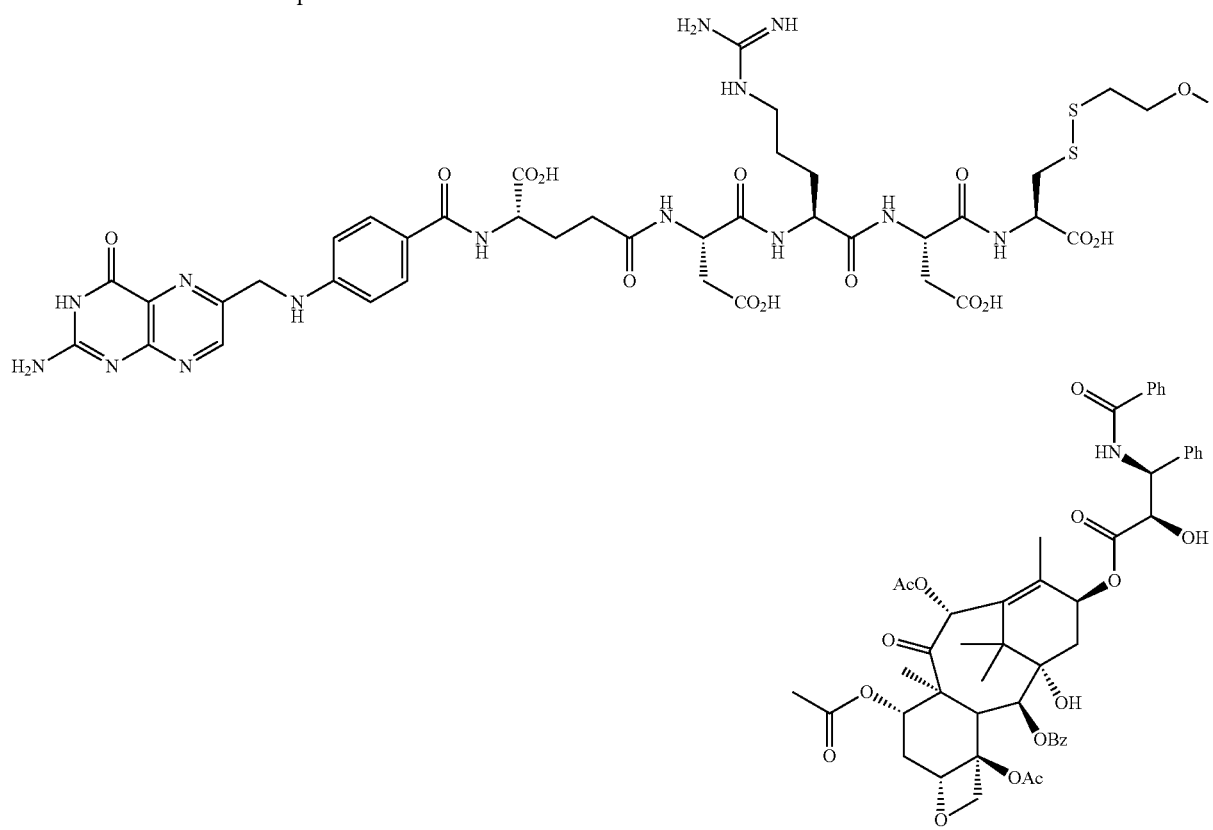
$^1$H NMR (DMSO-$d_6$/D$_2$O) δ 1.0 (s, 1H), 1.1 (s, 1H), 1.65 (s, 1H), 2.1 (s, 1H), 2.25 (s, 3H), 2.6 (dd, 2H), 3.25 (dd, 1H), 3.6 (t, 2H), 3.7 (d, 1H), 4.4 (t, 1H), 4.6 (d, 1H), 4.95 (d, 1H), 5.9 (t, 1H), 6.2 (s, 1H), 6.6 (d, 2H), 7.7 (t, 1H), 7.9 (d, 2H), 7.95 (d, 2H), 8.6 (s, 1H), 9.1 (d, 2H).
Example 6e
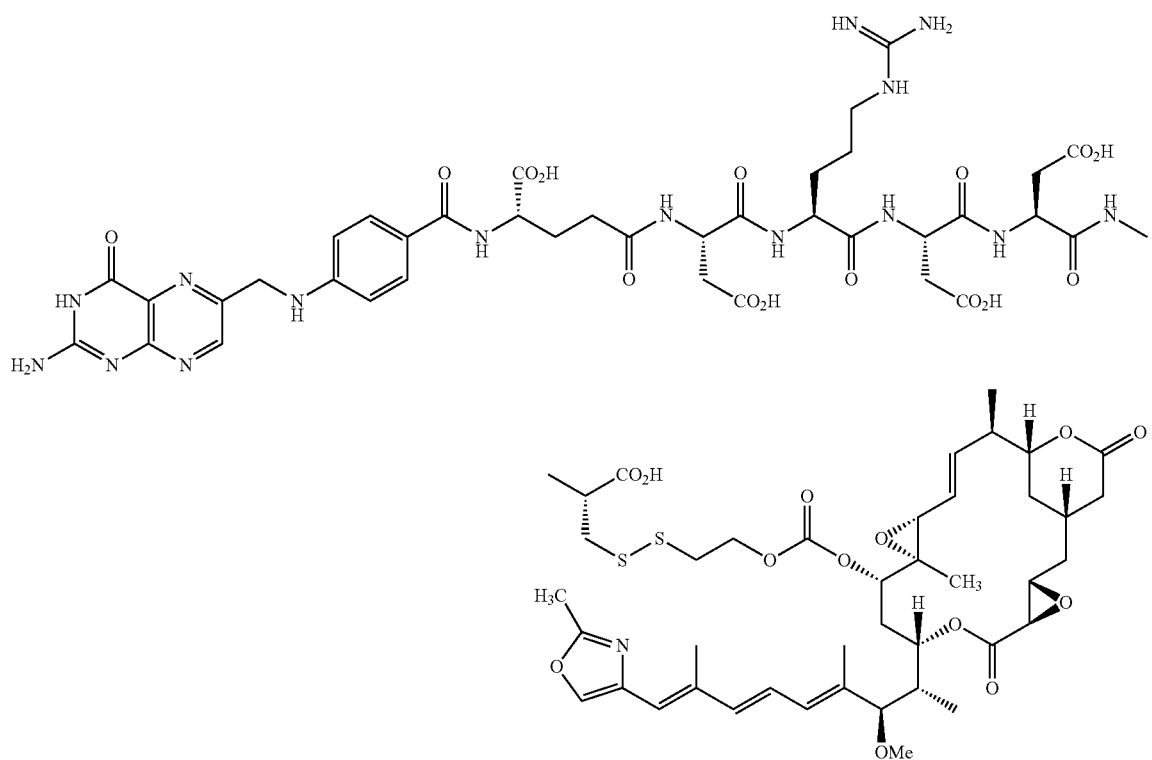

$^1$H NMR (DMSO-d$_6$/D$_2$O) δ 10.85 (d, 2H), 1.05 (d, 2H), 1.2 (d, 2H), 1.7 (d, 2H), 3.95 (d, 1H), 4.05 (dd, 1H), 5.4 (dd, 1H), 5.7 (dd, 1H), 6.65 (d, 2H), 7.6 (d, 2H), 7.95 (s, 1H), 8.65 (s, 1H).
Example 6f
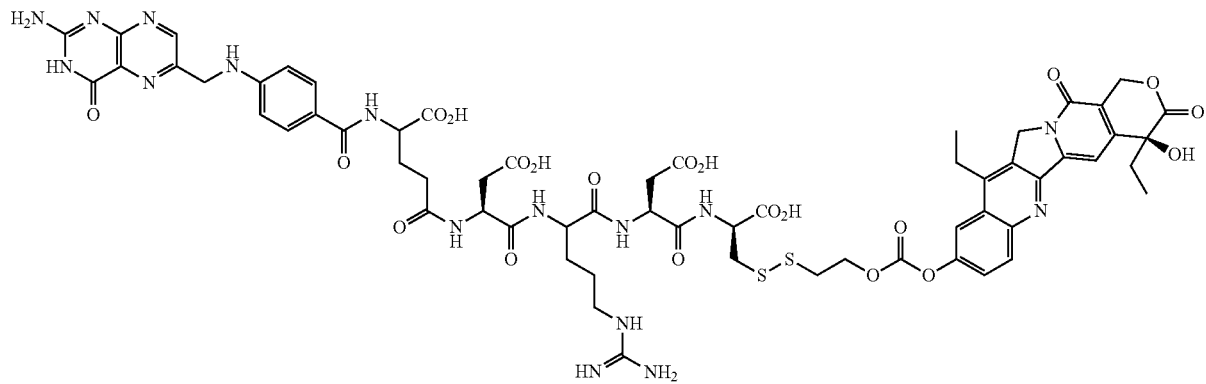 [SMILES: CCc1c2c(nc3ccc(OC(=O)OCCSSC[C@@H](NC(=O)[C@H](CC(=O)O)NC(=O)C(CCCNC(=N)N)NC(=O)[C@H](CC(=O)O)NC(=O)CCC(NC(=O)c4ccc(NCc5cnc6nc(N)[nH]c(=O)c6n5)cc4)C(=O)O)C(=O)O)cc13)-c1cc3c(c(=O)n1C2)COC(=O)[C@]3(O)CC]
ES MS (m+H)$^+$ 1487.23; $^1$H NMR (DMSO-d$_6$/D$_2$O) δ0.9 (t, 2H), 1.3 (t, 2H), 2.15 (t, 2H), 3.2 (dd, 1H), 4.0 (t, 1H), 4.15 (q, 1H), 5.3 (s, 2H), 5.5 (s, 2H), 6.6 (d, 2H), 7.0 (s, 1H), 7.4 (m, 2H), 7.55 (d, 2H), 8.0 (d, 2H), 8.6 (s, 1 H).
Example 7
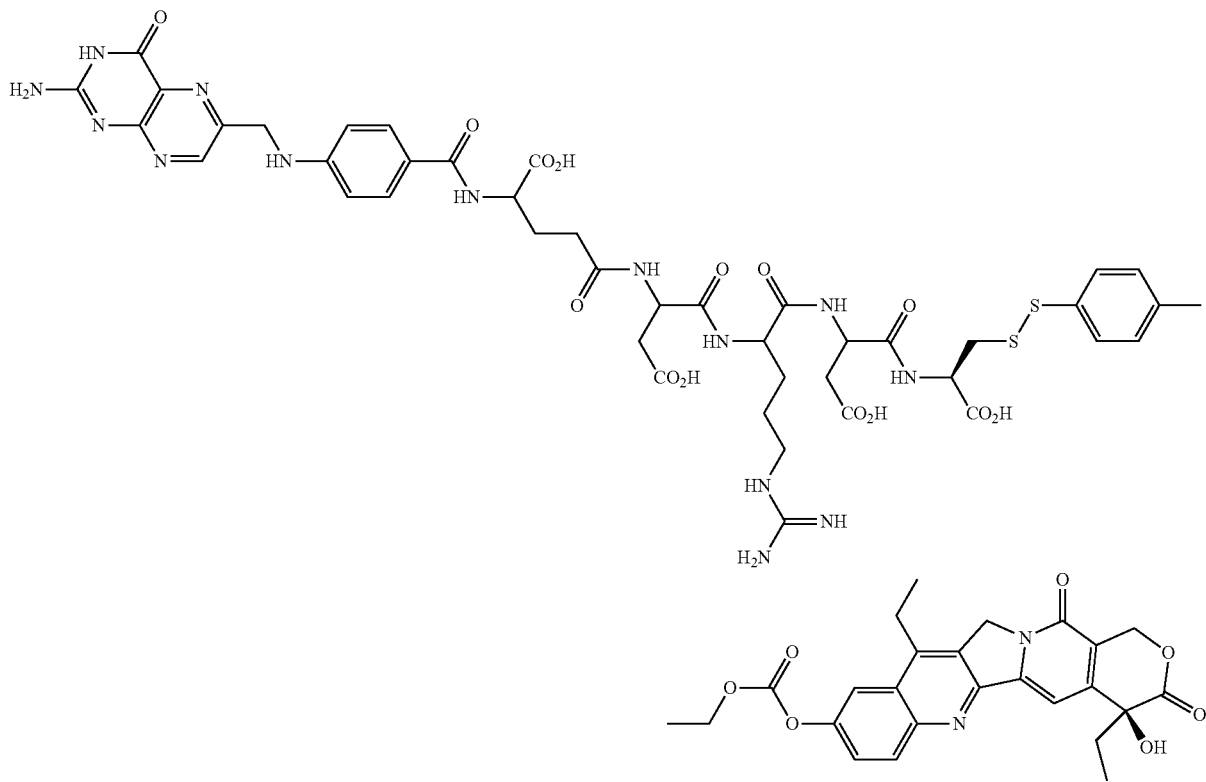

The intermediate 4-(2-pyridinyldithio)benzylcarbonate of SN 38 (10-hydroxy-7-ethylcamptothecin) was prepared according to the procedure described by P. Senter et al., *J. Org. Chem.* 1990, 55, 2875, the disclosure of which is incorporated herein by reference. The peptidyl fragmant Pte-Glu-Asp-Arg-Asp-Cys-OH, prepared as described herein, was dissolved in DMSO, and to the resulting clear yellow solution was added the pyridyl-dithio derivatized drug. After 30 min, the reaction was completed and the conjugate purified by HPLC; ES MS (m+H)+ 1425.38; $^1$H NMR (DMSO-$d_6$/$D_2O$) δ 0.9 (t), 1.15 (t), 3.9 (t), 4.0 (t), 4.25 (t), 5.1 (m), 5.2 (s), 5.4 (s), 6.55 (d), 7.25 (d), 7.35 (d), 7.5 (d), 7.9 (d), 8.55 (s).

Example 8

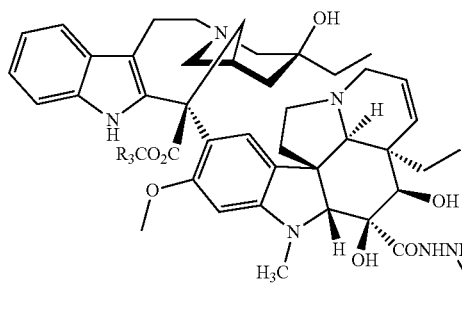
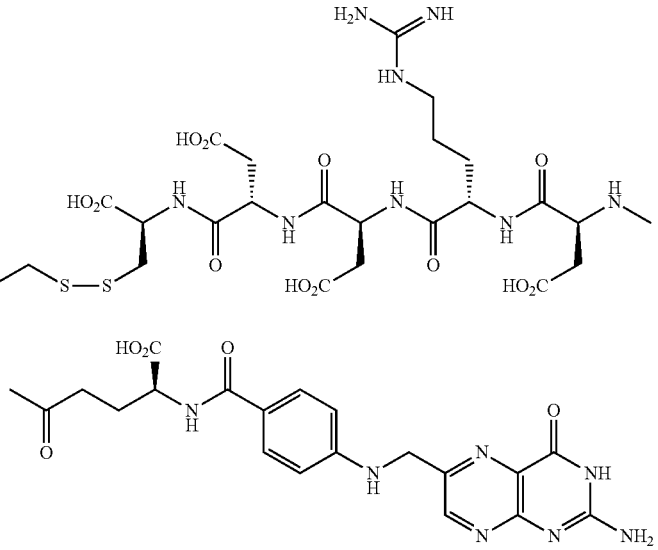

The compound of Example 8 was prepared from the peptidyl fragment Pte-Glu-Asp-Arg-Asp-Asp-Cys-OH , prepared according to the procedures described herein and alternatively by conventional procedures, such as those described in U.S. Patent Application Publication No. US-2005-0002942-A1. The peptidyl fragment also reacted with either the thiosulfonate or pyridyldithio-activated vinblastine to form Example 8. The pyridyldithio-activated vinblastine intermediates were prepared using the procedures described herein for other examples.

Examples 9-13

The compounds of Examples 9-13 were prepared according to the procedures generally described herein, and were characterized by electrospray mass spectroscopy (ES MS), and other spectroscopic techniques, including 1D and 2D NMR, and UV, illustrative results of which are described herein.

Example 9

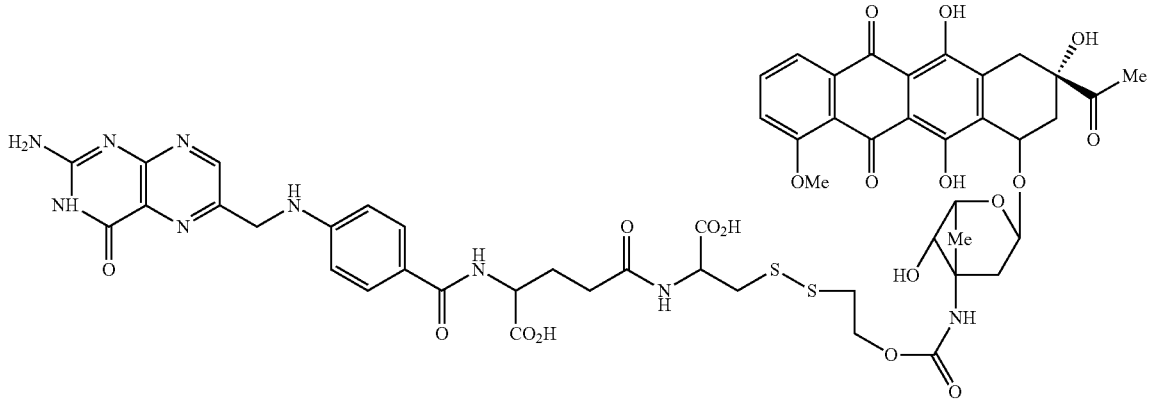

UV (nm) 233 (max), 255, 280; $^1$H NMR (D$_2$O, NaOD, CD$_3$CN) δ 1.15 (d, 3H), 2.3 (s, 3H), 3.6 (s, 1H), 3.85 (s, 3H), 4.9 (s, 1H), 5.3 (s, 1H), 6.5 (d, 2H), 7.3 (m, 1H), 7.5 (d, 2H), 7.65 (d, 2H), 8.4 (s, 1H).
Example 10
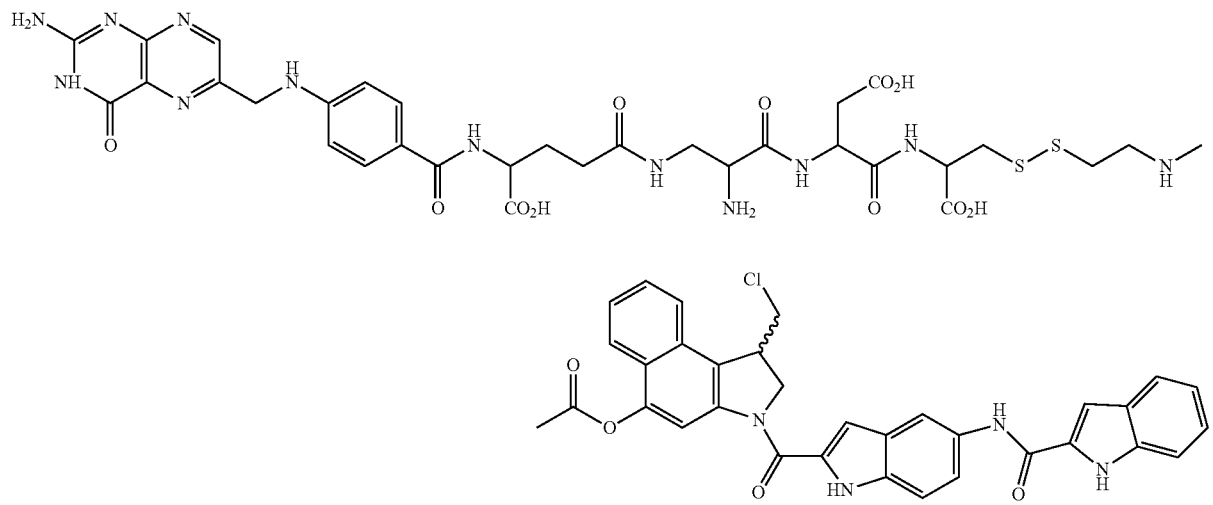
ES MS (m+H)$^+$ 1382.3, (m+Na)$^+$ 1405.4.
Example 11
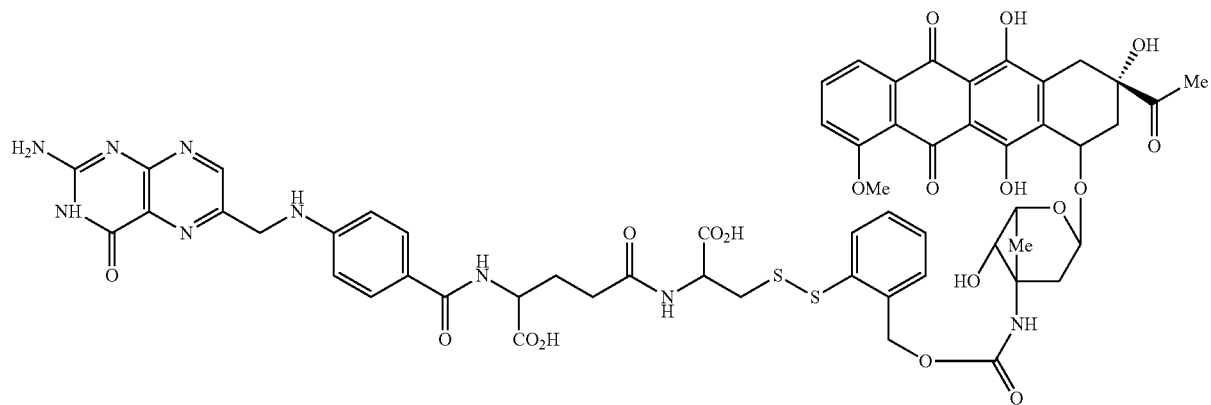
Example 12
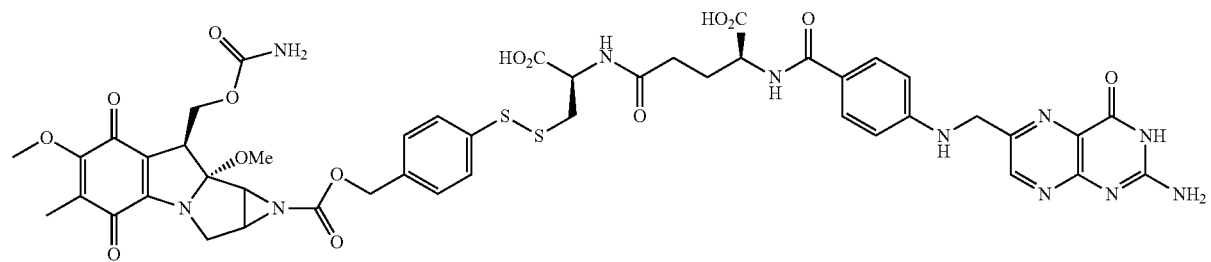 [SMILES: COC1=C(C)C(=O)C2=C(C1=O)[C@@H](COC(N)=O)[C@@]1(OC)C3C(CN21)N3C(=O)OCc1ccc(SSC[C@H](NC(=O)CC[C@H](NC(=O)c2ccc(NCc3cnc4nc(N)[nH]c(=O)c4n3)cc2)C(=O)O)C(=O)O)cc1]

Example 13

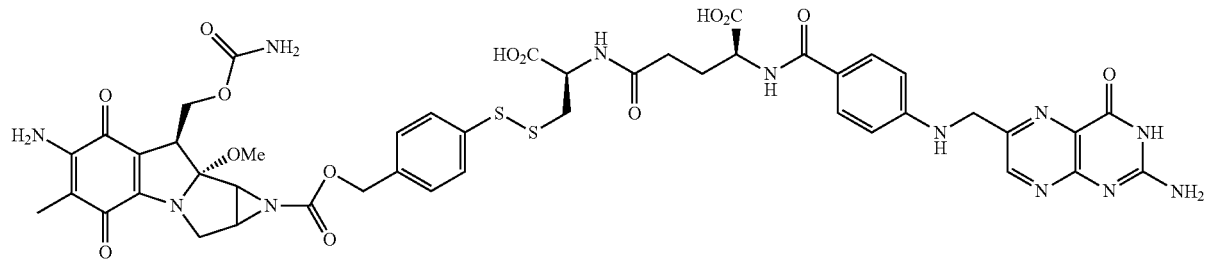 [SMILES: CO[C@]12C3C(CN1C1=C(C(=O)C(N)=C(C)C1=O)[C@H]2COC(N)=O)N3C(=O)OCc1ccc(SSC[C@H](NC(=O)CC[C@H](NC(=O)c2ccc(NCc3cnc4nc(N)[nH]c(=O)c4n3)cc2)C(=O)O)C(=O)O)cc1]

The foregoing exemplary embodiments are intended to be illustrative of the invention, and should not be interpreted or construed as limiting in any way the invention as described herein. For example, compounds generally represented by the following illustrative vitamin-drug conjugate are to be included in the invention as described herein

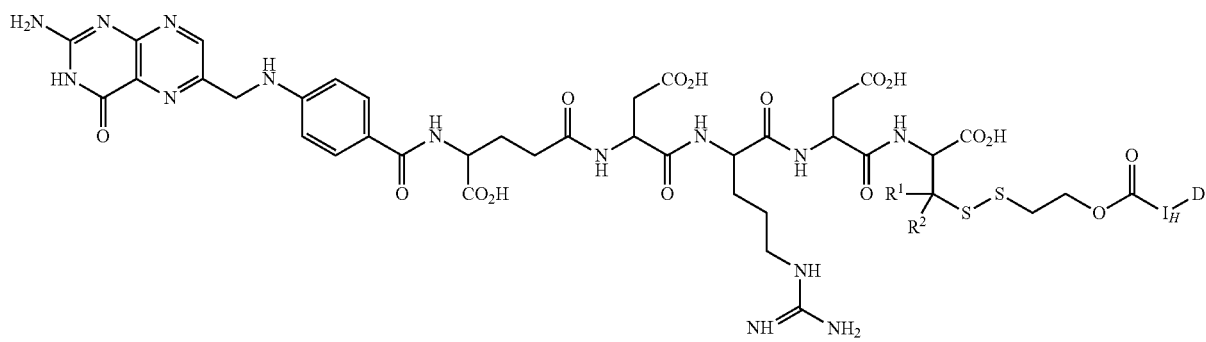

where $R^1$ and $R^2$ are each independently hydrogen or alkyl, such as methyl; and $I_H$ is a heteroatom, such as oxygen, sulfur, optionally substituted nitrogen, or optionally protected nitrogen, and the like.

The invention claimed is:
1. A compound of the formula

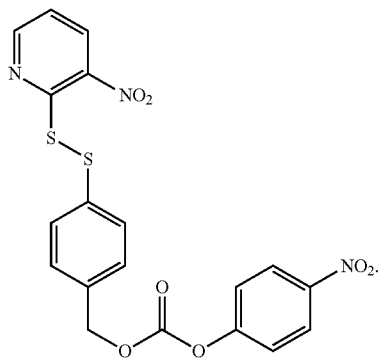 [SMILES: O=C(OCc1ccc(SSc2ncccc2[N+](=O)[O-])cc1)Oc1ccc([N+](=O)[O-])cc1]

* * * * *